US010722174B2

(12) United States Patent
Pang et al.

(10) Patent No.: US 10,722,174 B2
(45) Date of Patent: Jul. 28, 2020

(54) SKIN-CONFORMAL SENSORS

(71) Applicant: The Board of Trustees of the Leland Stanford Junior University, Palo Alto, CA (US)

(72) Inventors: Changhyun Pang, Suwon (KR); Zhenan Bao, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 141 days.

(21) Appl. No.: 14/796,800

(22) Filed: Jul. 10, 2015

(65) Prior Publication Data
US 2016/0051195 A1 Feb. 25, 2016

Related U.S. Application Data

(60) Provisional application No. 62/023,684, filed on Jul. 11, 2014.

(51) Int. Cl.
A61B 5/00 (2006.01)
A61B 5/0205 (2006.01)
A61B 5/024 (2006.01)
A61B 5/0402 (2006.01)
A61B 5/0476 (2006.01)
A61B 5/01 (2006.01)

(52) U.S. Cl.
CPC .......... *A61B 5/6833* (2013.01); *A61B 5/0002* (2013.01); *A61B 5/02055* (2013.01); *A61B 5/02444* (2013.01); *A61B 5/0402* (2013.01); *A61B 5/01* (2013.01); *A61B 5/0476* (2013.01); *A61B 5/7246* (2013.01); *A61B 2562/028* (2013.01); *A61B 2562/0247* (2013.01)

(58) Field of Classification Search
CPC . A61B 5/6833; A61B 5/0402; A61B 5/02055; A61B 5/0476; A61B 5/0002; A61B 5/02427; A61B 2562/0247; A61B 2562/028
See application file for complete search history.

(56) References Cited

U.S. PATENT DOCUMENTS

| 4,314,227 A | 2/1982 | Eventoff |
| 5,302,936 A | 4/1994 | Yaniger |
| 5,989,700 A | 11/1999 | Krivopal |
| 6,589,629 B1 | 7/2003 | Bao et al. |
| 7,137,291 B2 | 11/2006 | Mancevski |

(Continued)

OTHER PUBLICATIONS

Changhyun Pang, Won-Gyu Bae, Hong Nam Kim and Kahp-Yang Suh. "Wearable skin sensors for in vitro diagnostics" Dec. 3, 2012, SPIE Newsroom. DOI: 10.1117/2.1201211.004554.*

(Continued)

*Primary Examiner* — Nathan J Jenness
(74) *Attorney, Agent, or Firm* — Crawford Maunu PLLC

(57) ABSTRACT

Various aspects as described herein are directed to skin-conformal sensor devices and methods of using the same. As consistent with one or more embodiments, a sensor device includes an upper portion and lower portion. The upper portion includes a plurality of layers including at least one sensor. The lower portion includes a layer of microstructures configured and arranged to interface with skin of a subject and to interlock the skin with the at least one sensor.

15 Claims, 15 Drawing Sheets

(56) References Cited

U.S. PATENT DOCUMENTS

| | | | |
|---|---|---|---|
| 7,785,704 | B2 | 8/2010 | Papakostas et al. |
| 8,020,456 | B2 | 9/2011 | Liu et al. |
| 8,161,826 | B1 | 4/2012 | Taylor |
| 2003/0062652 | A1* | 4/2003 | Lee ............... B29C 33/3842 264/227 |
| 2005/0148984 | A1* | 7/2005 | Lindsay ............ A61F 13/5611 604/387 |
| 2006/0260417 | A1 | 11/2006 | Son et al. |
| 2011/0034328 | A1 | 2/2011 | Kang et al. |
| 2011/0108936 | A1 | 5/2011 | Meng et al. |
| 2011/0192233 | A1 | 8/2011 | Aizenberg et al. |
| 2012/0062245 | A1 | 3/2012 | Bao et al. |
| 2012/0177934 | A1 | 7/2012 | Vogel et al. |
| 2012/0301607 | A1 | 11/2012 | Kabir et al. |
| 2013/0211310 | A1* | 8/2013 | Bommarito ............ B08B 17/06 602/48 |
| 2015/0059486 | A1* | 3/2015 | Choong ................ G01L 9/0052 73/727 |

OTHER PUBLICATIONS

Moon Kyu Kwak, Hoon-Eui Jeong, Kahp Y. Su. "Rational Design and Enhanced Biocompatibility of a Dry Adhesive Medical Skin Patch" Adv. Mat. vol. 23, Issue 34 Sep. 8, 2011 pp. 3949-3395.*

Choong et al. "Highly Stretchable Resistive Pressure Sensors Using a Conductive Elastomeric Composite on a Micropyramid Array" Adv. Mater. Feb. 17, 2014, 26, 3451-3458.*

Campo et al. "Contact Shape Controls Adhesion of Bioinspired Fibrillar Surfaces" Langmuir 2007, 23, 10235-10243.*

Carbone et al. "A review of adhesion mechanisms of mushroom-shaped microstructured adhesives" Meccanica (Mar. 19, 2013) 48:1819-1833.*

Pang et al. "A flexible and highly sensitive strain-gauge sensor using reversible interlocking of nanofibres" Nature Materials 11,795-801 (2012).*

Pantelopoulos, Alexandros, and Nikolaos G. Bourbakis. "A survey on wearable sensor-based systems for health monitoring and prognosis." Systems, Man, and Cybernetics, Part C: Applications and Reviews, IEEE Transactions on 40.1 (2010): 1-12.

Zhang, Da Ren, et al. "A wireless ECG plaster for real-time cardiac health monitoring in body sensor networks." Biomedical Circuits and Systems Conference (BioCAS), 2011 IEEE. IEEE, 2011.

Zhu, Guang, et al. "Triboelectric-generator-driven pulse electrodeposition for micropatterning." Nano letters 12.9 (2012): 4960-4965.

Que, Ronghui, et al. "Flexible nanogenerators based on graphene oxide films for acoustic energy harvesting." Angewandte Chemie 124.22 (2012): 5514-5518. Abstract Only.

Hinchet, Ronan, et al. "Performance Optimization of Vertical Nanowire—based Piezoelectric Nanogenerators." Advanced Functional Materials 24.7 (2014): 971-977.

Lee, Keun Young, et al. "P-Type polymer-hybridized high-performance piezoelectric nanogenerators." Nano letters 12.4 (2012): 1959-1964.

Yu, Zhibin, et al. "Highly Flexible Silver Nanowire Electrodes for Shape—Memory Polymer Light—Emitting Diodes." Advanced Materials 23.5 (2011): 664-668. Abstract Only.

Xu, Feng, and Yong Zhu. "Highly conductive and stretchable silver nanowire conductors." Advanced Materials 24.37 (2012): 5117-5122.

Park, Minwoo, et al. "Highly stretchable electric circuits from a composite material of silver nanoparticles and elastomeric fibres." Nature nanotechnology 7.12 (2012): 803-809. Abstract Only.

Feng, Xue, et al. "Stretchable ferroelectric nanoribbons with wavy configurations on elastomeric substrates." Acs Nano 5.4 (2011): 3326-3332.

Bauer, Siegfried, Reimund Gerhard-Multhaupt, and Gerhard M. Sessler. "Ferroelectrets: Soft electroactive foams for transducers." Physics Today 57.2 (2004): 37-43. Abstract Only.

Zhang, Xiaoqing, et al. "Piezoelectric properties of irradiation-crosslinked polypropylene ferroelectrets." Applied Physics Letters 91.18 (2007): 2901. Abstract Only.

Zhang, Xiaoqing, et al. "Quasi-static and dynamic piezoelectric d 33 coefficients of irradiation cross-linked polypropylene ferroelectrets." Journal of materials science 44.10 (2009): 2459-2465. Abstract Only.

Wegener, M., et al. "Controlled inflation of voids in cellular polymer ferroelectrets: Optimizing electromechanical transducer properties." Applied Physics Letters 84.3 (2004): 392-394.

Neugschwandtner, G. S., et al. "Large and broadband piezoelectricity in smart polymer-foam space-charge electrets." Applied Physics Letters 77.23 (2000): 3827-3829. Abstract Only.

Mellinger, Axel. "Dielectric resonance spectroscopy: a versatile tool in the quest for better piezoelectric polymers." Dielectrics and Electrical Insulation, IEEE Transactions on 10.5 (2003): 842-861. Abstract Only.

Hillenbrand, J., and G. M. Sessler. "Piezoelectricity in cellular electret films." Dielectrics and Electrical Insulation, IEEE Transactions on 7.4 (2000): 537-542. Abstract Only.

Sessler, G. M., and J. Hillenbrand. "Electromechanical response of cellular electret films." Applied Physics Letters 75.21 (1999): 3405-3407. Abstract Only.

Qi, Yi, et al. "Enhanced piezoelectricity and stretchability in energy harvesting devices fabricated from buckled PZT ribbons." Nano letters 11.3 (2011): 1331-1336.

Ko, Hyunhyub, et al. "Multifunctional, flexible electronic systems based on engineered nanostructured materials." Nanotechnology 23.34 (2012): 344001.

Gao, Qiang, et al. "Flexible tactile sensor using the reversible deformation of poly (3-hexylthiophene) nanofiber assemblies." Langmuir 28.51 (2012): 17593-17596.

Maheshwari, Vivek, and Ravi F. Saraf. "High-resolution thin-film device to sense texture by touch." Science 312.5779 (2006): 1501-1504.

Segev-Bar, Meital, et al. "Tunable touch sensor and combined sensing platform: toward nanoparticle-based electronic skin." ACS applied materials & interfaces 5.12 (2013): 5531-5541. Abstract Only.

Yao, Hong—Bin, et al. "A flexible and highly pressure—sensitive graphene—polyurethane sponge based on fractured microstructure design." Advanced Materials 25.46 (2013): 6692-6698. Abstract Only.

Liu, Xinchuan, et al. "A highly sensitive pressure sensor using a Au-patterned polydimethylsiloxane membrane for biosensing applications." Journal of Micromechanics and Microengineering 23.2 (2013): 025022.

Choong, Chwee—Lin, et al. "Highly stretchable resistive pressure sensors using a conductive elastomeric composite on a micropyramid array." Advanced Materials 26.21 (2014): 3451-3458.

Cai, Le, et al. "Super-stretchable, transparent carbon nanotube-based capacitive strain sensors for human motion detection." Scientific reports 3 (2013).

Lin, Lin, et al. "Towards tunable sensitivity of electrical property to strain for conductive polymer composites based on thermoplastic elastomer." ACS applied materials & interfaces 5.12 (2013): 5815-5824. Abstract Only.

Cohen, Daniel J., et al. "A highly elastic, capacitive strain gauge based on percolating nanotube networks." Nano letters 12.4 (2012): 1821-1825. Abstract Only.

Matsuzaki, Ryosuke, et al. "Rubber-based strain sensor fabricated using photolithography for intelligent tires." Sensors and Actuators A: Physical 148.1 (2008): 1-9.

Xiao, Xu, et al. "High—Strain Sensors Based on ZnO Nanowire/ Polystyrene Hybridized Flexible Films." Advanced Materials 23.45 (2011): 5440-5444.

Cha, Seung Nam, et al. "Sound—Driven Piezoelectric Nanowire—Based Nanogenerators." Advanced materials 22.42 (2010): 4726-4730.

Wang, Xudong, et al. "Direct-current nanogenerator driven by ultrasonic waves." Science 316.5821 (2007): 102-105.

(56) References Cited

OTHER PUBLICATIONS

Wang, Zhong Lin, and Jinhui Song. "Piezoelectric nanogenerators based on zinc oxide nanowire arrays." Science 312.5771 (2006): 242-246.
Kim, Hyunjin, et al. "Enhancement of piezoelectricity via electrostatic effects on a textile platform." Energy & Environmental Science 5.10 (2012): 8932-8936. Abstract Only.
Xu, Sheng, et al. "Self-powered nanowire devices." Nature nanotechnology 5.5 (2010): 366-373.
Chang, Chieh, et al. "Direct-write piezoelectric polymeric nanogenerator with high energy conversion efficiency." Nano letters 10.2 (2010): 726-731.
Cha, SeungNam, et al. "Porous PVDF as effective sonic wave driven nanogenerators." Nano letters 11.12 (2011): 5142-5147.
Chang, Jiyoung, et al. "Piezoelectric nanofibers for energy scavenging applications." Nano Energy 1.3 (2012): 356-371.
Lee, Ju—Hyuck, et al. "Highly Stretchable Piezoelectric—Pyroelectric Hybrid Nanogenerator." Advanced Materials 26.5 (2014): 765-769.
Park, Kwi—II, et al. "Flexible nanocomposite generator made of BaTiO3 nanoparticles and graphitic carbons." Advanced Materials 24.22 (2012): 2999-3004.
Wu, Wenzhuo, Xiaonan Wen, and Zhong Lin Wang. "Taxel-addressable matrix of vertical-nanowire piezotronic transistors for active and adaptive tactile imaging." Science 340.6135 (2013): 952-957.
Fan, Feng-Ru, et al. "Transparent triboelectric nanogenerators and self-powered pressure sensors based on micropatterned plastic films." Nano letters 12.6 (2012): 3109-3114.
Lin, Long, et al. "Triboelectric active sensor array for self-powered static and dynamic pressure detection and tactile imaging." ACS nano 7.9 (2013): 8266-8274.
Lin, Zong-Hong, et al. "Enhanced Triboelectric Nanogenerators and Triboelectric Nanosensor Using Chemically Modified TiO2 Nanomaterials." ACS nano 7.5 (2013): 4554-4560.
Yang, Ya, et al. "Human skin based triboelectric nanogenerators for harvesting biomechanical energy and as self-powered active tactile sensor system." ACS nano 7.10 (2013): 9213-9222.
Yang, Ya, et al. "Electret Film-Enhanced Triboelectric Nanogenerator Matrix for Self-Powered Instantaneous Tactile Imaging." ACS applied materials & interfaces 6.5 (2014): 3680-3688.
Sekitani, Tsuyoshi, and Takao Someya. "Stretchable, Large—area Organic Electronics." Advanced Materials 22.20 (2010): 2228-2246. Abstract Only.
Rogers, John A., Takao Someya, and Yonggang Huang. "Materials and mechanics for stretchable electronics." Science 327.5973 (2010): 1603-1607.
Mi, Yongli, et al. "Micromolding of PDMS scaffolds and microwells for tissue culture and cell patterning: A new method of microfabrication by the self-assembled micropatterns of diblock copolymer micelles." Polymer 47.14 (2006): 5124-5130.
Balaban, Nathalie Q., et al. "Force and focal adhesion assembly: a close relationship studied using elastic micropatterned substrates." Nature cell biology 3.5 (2001): 466-472.
Sekitani, Tsuyoshi, et al. "A rubberlike stretchable active matrix using elastic conductors." Science 321.5895 (2008): 1468-1472. Abstract Only.
Wang, Sihong, Long Lin, and Zhong Lin Wang. "Nanoscale triboelectric-effect-enabled energy conversion for sustainably powering portable electronics." Nano letters 12.12 (2012): 6339-6346.
Hu, Youfan, et al. "Triboelectric nanogenerator built on suspended 3D spiral structure as vibration and positioning sensor and wave energy harvester." ACS nano 7.11 (2013): 10424-10432.
Yang, Jin, et al. "Triboelectrification-based organic film nanogenerator for acoustic energy harvesting and self-powered active acoustic sensing." ACS nano 8.3 (2014): 2649-2657.
Zhu, Guang, et al. "Toward large-scale energy harvesting by a nanoparticle-enhanced triboelectric nanogenerator." Nano letters 13.2 (2013): 847-853.

Bai, Peng, et al. "Integrated multilayered triboelectric nanogenerator for harvesting biomechanical energy from human motions." Acs Nano 7.4 (2013): 3713-3719.
Zhong, Junwen, et al. "Finger typing driven triboelectric nanogenerator and its use for instantaneously lighting up LEDs." Nano Energy 2A (2013): 491-497. Abstract Only.
Zhang, Xiao-Sheng, et al. "Frequency-multiplication high-output triboelectric nanogenerator for sustainably powering biomedical microsystems." Nano letters 13.3 (2013): 1168-1172. Abstract Only.
Wang, Sihong, et al. "Freestanding Triboelectric—Layer—Based Nanogenerators for Harvesting Energy from a Moving Object or Human Motion in Contact and Non—contact Modes." Advanced Materials 26.18 (2014): 2818-2824.
Cheng, Gang, et al. "Increase Output Energy and Operation Frequency of a Triboelectric Nanogenerator by Two Grounded Electrodes Approach." Advanced Functional Materials 24.19 (2014): 2892-2898.
Lin, Long, et al. "Segmentally structured disk triboelectric nanogenerator for harvesting rotational mechanical energy." Nano letters 13.6 (2013): 2916-2923.
Wang, Zhong Lin. "Triboelectric nanogenerators as new energy technology for self-powered systems and as active mechanical and chemical sensors." ACS nano 7.11 (2013): 9533-9557.
Wang, Sihong, et al. "Sliding-triboelectric nanogenerators based on in-plane charge-separation mechanism." Nano letters 13.5 (2013): 2226-2233.
Surapaneni, R., et al. "A three-axis high-resolution capacitive tactile imager system based on floating comb electrodes." Journal of Micromechanics and Microengineering 23.7 (2013): 075004. Abstract Only.
Liao, K. W., Max T. Hou, and J. Andrew Yeh. "A dielectiric liquid-based capcitive tactile sensor for normal and shear force sensing." Solid-State Sensors, Actuators and Microsystems (Transducers & Eurosensors XXVII), 2013 Transducers & Eurosensors XXVII: The 17th International Conference on. IEEE, 2013. Abstract Only.
Dobrzynska, Jagoda Anna, and M. A. M. Gijs. "Polymer-based flexible capacitive sensor for three-axial force measurements." Journal of Micromechanics and Microengineering 23.1 (2013): 015009. Abstract Only.
Lee, Hyung-Kew, et al. "Real-time measurement of the three-axis contact force distribution using a flexible capacitive polymer tactile sensor." Journal of Micromechanics and Microengineering 21.3 (2011): 035010.
Deepu, Chacko John, et al. "An ECG-on-chip for wearable cardiac monitoring devices." Electronic Design, Test and Application, 2010. DELTA'10. Fifth IEEE International Symposium on. IEEE, 2010.
Yu, Z. B., Niu, X. F., Liu, Z. & Pei, Q. B. "Intrinsically stretchable polymer light-emitting devices using carbon nanotube-polymer composite electrodes", Adv. Mater. 23, 3989-3994 (2011). Abstract Only.
Ilievski, F., Mazzeo, A. D., Shephard, R. F., Chen, X. & Whitesides, G.M. "Soft robotics for chemists". Angew. Chem. Int. Ed. 50, 1890-1895 (2011).
Zhu and Xu "Buckling of Aligned Carbon Nanotubes as Stretchable Conductors: A New Manufacturing Strategy"; Adv. Mater. 2012, 24, 1073-1077.
Xu et al. "Wavy Ribbons of Carbon Nanotubes for Stretchable Conductors" Adv. Funct. Mater. 2012.
Akter et al. "Reversible Stretchable Transparent Conductive Coatings of Spray-Deposited Silver Nanowires"; ACS Appl. Mater. Interfaces, 2012, 4(4), pp. 1855-1859. Abstract Only.
Xu et al., "Highly Conductive and Stretchable Silver Nanowire Conductors"; Adv. Mater. 2012, 24, 5117-5122.
Kim et al., "Single-walled carbon nanotube/silicone rubber composites for compliant electrodes", SciVerse ScienceDirect, 2011.
Bergeron, "Stanford researchers build transparent, super-stretchy skin-like sensor", http://new.stanford.edu/pr/2011/pr-stretchy-skinlike-sensor-102411.html on Dec. 1, 2011.
Eberlein B., et al. "Skin surface pH, stratum corneum hydration, trans-epidermal water loss and skin roughness related to atopic eczema and skin dryness in a population of primary school children: clinical report." Acta Dermatology-Venerology 80 (2000): 188-191.

(56) References Cited

OTHER PUBLICATIONS

Conover, M. B. Understanding electrocardiography. (Mosby, 2002). Book Overview Provided.

Tafur, Emilio, Lawrence S. Cohen, and Harold D. Levine. "The Normal Apex Cardiogram Its Temporal Relationship to Electrical, Acoustic, and Mechanical Cardiac Events." Circulation 30.3 (1964): 381-391.

Pittman, James Al, John Sum Ping, and Jonathan B. Mark. "Arterial and central venous pressure monitoring." International anesthesiology clinics 42.1 (2004): 13-30.

Mannsfeld et al. "Highly sensitive flexible pressure sensors with microstructured rubber dielectric layers." (2010).

Ko H., et al., "Multifuctional flexible electronic systems based on engineered nanostructured materials," Nanotechnology 23 (2012).

Dahiya, Ravinder S., et al. "Tactile sensing—from humans to humanoids." Robotics, IEEE Transactions on 26.1 (2010): 1-20.

Pang, Changhyun, Chanseok Lee, and Kahp—Yang Suh. "Recent advances in flexible sensors for wearable and implantable devices." Journal of Applied Polymer Science 130.3 (2013): 1429-1441.

Takahashi, Toshitake, et al. "Carbon nanotube active-matrix backplanes for conformal electronics and sensors." Nano letters 11.12 (2011): 5408-5413.

Wang, Chuan, et al. "User-interactive electronic skin for instantaneous pressure visualization." Nature materials 12.10 (2013): 899-904.

Lee, Hyung-Kew, Sun-Il Chang, and Euisik Yoon. "A flexible polymer tactile sensor: Fabrication and modular expandability for large area deployment." Microelectromechanical Systems, Journal of 15.6 (2006): 1681-1686.

Cheng, M. Y., et al. "A flexible capacitive tactile sensing array with floating electrodes." Journal of Micromechanics and Microengineering 19.11 (2009): 115001.

Gong, Shu, et al. "A wearable and highly sensitive pressure sensor with ultrathin gold nanowires." Nature communications 5 (2014). Abstract Only.

Pan, Lijia, et al. "An ultra-sensitive resistive pressure sensor based on hollow-sphere microstructure induced elasticity in conducting polymer film." Nature communications 5 (2014).

Oaki, Y., Kijima, M., Imai, H. Synthesis and Morphogenesis of Organic Polymer Materials with Hierarchical Structures in Biominerals. J. Am. Chem. Soc.133, 8594-8599 (2011). Abstract Only.

Hillis, W. D. A high-resolution imaging touch sensor. Int. J. Robot. Res.1, 33-44 (1982). Abstract Only.

Barnoss, S., et al. Piezoresistance in chemically synthesized polypyrrole thin films. Sensor. Actuat. A-Phys.154, 79-84 (2009).

Scilingo, E. P., et al. Strain-sensing fabrics for wearable kinaesthetic-like systems. IEEE Sensor. J.3, 460-467 (2003).

Wu, J., et al. Conducting polymer coated lycra. Synth. Met.155, 698-701 (2005). Abstract Only.

Kim, D. H. et al. Epidermal Electronics. Science 333, 838-843 (2011).

Sokolov, A. N., Tee, B. C. K., Bettinger, C. J., Tok, J. B. H. & Bao, Z. Chemical and engineering approaches to enable organic field-effect transistors for electronic skin applications. Acc. Chem. Res. 45, 361-371 (2012). Abstract Only.

Wagner, S. & Bauer, S. Materials for stretchable electronics. MRS Bull. 37, 207-217 (2012).

Lumelsky, V. J., Shur, M. S. & Wagner, S. Sensitive skin. IEEE Sens. J. 1, 41-51 (2001).

Someya, T. et al. A large-area, flexible pressure sensor matrix with organic fieldeffect transistors for artificial skin applications. Proc. Natl Acad. Sci. USA 101, 9966-9970 (2004).

Mannsfeld, S. C. B. et al. Highly sensitive flexible pressure sensors with microstructured rubber dielectric layers. Nat. Mater. 9, 859-864 (2010).

Takei, K. et al. Nanowire active-matrix circuitry for low-voltage macroscale artificial skin. Nat. Mater. 9, 821-826 (2010).

Hu, W. L., Niu, X. F., Zhao, R. & Pei, Q. B. Elastomeric transparent capacitive sensors based on an interpenetrating composite of silver nanowires and polyurethane. Appl. Phys. Lett. 102, 083303 (2013).

Schwartz, G. et al. Flexible polymer transistors with high pressure sensitivity for application in electronic skin and health monitoring. Nat. Commun. 4, 1859-1859 (2013). Abstract Only.

Jeon, J., Lee, H.-B.-R. & Bao, Z. Flexible wireless temperature sensors based on Ni microparticle-filled binary polymer composites. Adv. Mater. 25, 850-855 (2013). Abstract Only.

Feng, J. et al. Giant moisture responsiveness of VS2 ultrathin nanosheets for novel touchless positioning interface. Adv. Mater. 24, 1969-1974 (2012). Abstract Only.

Tian, B. et al. Three-dimensional, flexible nanoscale field-effect transistors as localized bioprobes. Science 329, 830-834 (2010).

Viventi, J. et al. Flexible, foldable, actively multiplexed, high-density electrode array for mapping brain activity in vivo. Nat. Neurosci. 14, 1599-1605 (2011).

Roberts, M. E. et al. Water-stable organic transistors and their application in chemical and biological sensors. Proc. Natl Acad. Sci. USA 105, 12134-12139 (2008).

Li, D., Huang, J. & Kaner, R. B. Polyaniline nanofibers: a unique polymer nanostructure for versatile applications. Acc. Chem. Res. 42, 135-145 (2009).

Yamada, T. et al. A stretchable carbon nanotube strain sensor for humanmotion detection. Nat. Nanotechn. 6, 296-301 (2011).

Lipomi, D. J. et al. Skin-like pressure and strain sensors based on transparent elastic films of carbon nanotubes. Nat. Nanotechn. 6, 788-792 (2011). Abstract Only.

Pang, C. et al. A flexible and highly sensitive strain-gauge sensor using reversible interlocking of nanofibres. Nat. Mater. 11, 795-801 (2012).

Maheshwari, V. & Saraf, R. Tactile devices to sense touch on a par with a human finger. Angew. Chem. Int. Edit. 47, 7808-7826 (2008). Abstract Only.

Tee, B. C. K., Wang, C., Allen, R. & Bao, Z. An electrically and mechanically self-healing composite with pressure- and flexion-sensitive properties for electronic skin applications. Nat. Nanotechn. 7, 825-832 (2012). Abstract Only.

Wang, L. & Li, Y. A review for conductive polymer piezoresistive composites and a development of a compliant pressure transducer. IEEE Trans. Instru. Measu. 62, 495-502 (2013).

Hatzivasiliou, F. V. & Tzafestas, S. G. Analysis and design of a new piezoresistive tactile sensor system for robotic applications. J. Intell. Robot. Syst. 10, 243-256 (1994).

Ferguson-Pell, M., Hagisawa, S. & Bain, D. Evaluation of a sensor for low interface pressure applications. Med. Eng. Phys. 22, 657-663 (2000). Abstract Only.

Rosenberg, I. & Perlin, K. The UnMousePad—an interpolating multi-touch force-sensing input pad. ACM Trans. Graph. 28, 65 (2009).

Shan, Z. W. et al. Ultrahigh stress and strain in hierarchically structured hollow nanoparticles. Nat. Mater. 7, 947-952 (2008).

Mahmoud, W. E., El-Eraki, M. H. I., El-Lawindy, A. M. Y. & Hassan, H. H. A novel application of ADC/K-foaming agent-loaded NBR rubber composites as pressure sensor. J. Phys. D-Appl. Phys. 39, 541-546 (2006).

Brady, S., Diamond, D. & Lau, K. T. Inherently conducting polymer modified polyurethane smart foam for pressure sensing. Sensor Actuat. A-Phys. 119,398-404 (2005).

Metzger, C. et al. Flexible-foam-based capacitive sensor arrays for object detection at low cost. Appl. Phys. Lett. 92, 013506 (2008).

Piepenbrock, M.-O. M., Lloyd, G. O., Clarke, N. & Steed, J. W. Metal- and anion-binding supramolecular gels. Chem. Rev. 110, 1960-2004 (2010). First Page Only.

Yulia Galagan et al. Technology development for roll-to-roll production of organic photovoltaics. Chem. Eng. Process 50, 454-461 (2011). Abstract Only.

Kim, K. H., Oh, Y. & Islam, M. F. Graphene coating makes carbon nanotube aerogels superelastic and resistant to fatigue. Nat. Nanotechn. 7, 562-566 (2012).

Gorce, J. N., Hellgeth, J. W. & Ward, T. C. Mechanical hysteresis of a polyether polyurethane thermoplastic elastomer. Polym. Eng. Sci. 33, 1170-1176 (1993). Abstract Only.

Etchessahar, M. & Sahraoui, S. Frequency dependence of elastic properties of acoustic foams. J. Acoust. Soc. Am. 117, 1114-1121 (2005). Abstract Only.

(56) References Cited

OTHER PUBLICATIONS

Ahankari, S. S. & Kar, K. K. Hysteresis measurements and dynamic mechanical characterization of functionally graded natural rubber-carbon black composites. Polym. Eng. Sci. 50, 871-877 (2010). Abstract Only.

Shastry, V. V., Ramamurty, U. & Misra, A. Thermo-mechanical stability of a cellular assembly of carbon nanotubes in air. Carbon N. Y. 50, 4373-4378 (2012). Abstract Only.

Sanchez-Coronado, J. & Chung, D. D. L. Thermomechanical behavior of a graphite foam. Carbon N. Y. 41, 1175-1180 (2003).

Timsit, R. S. Electrical contact resistance: properties of stationary interfaces. IEEE Trans. Comp. Pack. Tech. 22, 85-98 (1999). Abstract Only.

Barnoss, S., Shanak, H., Bufon, C. C. B. & Heinzel, T. Piezoresistance in chemically synthesized polypyrrole thin films. Sensor Actuat. A-Phys. 154, 79-84 (2009).

Scilingo, E. P., Lorussi, F., Mazzoldi, A. & De Rossi, D. Strain-sensing fabrics for wearable kinaesthetic-like systems. IEEE Sensor. J. 3, 460-467 (2003).

Greenwood, J. A. & Williams, J. B. Contact of nominally flat surfaces. Proc. R. Soc. Lond. A 295, 300-319 (1966).

Archard, J. F. Elastic deformation and the laws of friction. Proc. R. Soc. Lond. A 243, 190-205 (1957).

Greenwood, J. A. Constriction resistance and the real area of contact. Br. J. Appl. Phys. 17, 1621-1632 (1966).

Lau, Y. Y. & Tang, W. A higher dimensional theory of electrical contact resistance. J. Appl. Phys. 105, 124902 (2009). Abstract Only.

Gomez, M. R. et al. Experimental validation of a higher dimensional theory of electrical contact resistance. Appl. Phys. Lett. 95, 072103 (2009).

Zhang, P. & Lau, Y. Y. Scaling laws for electrical contact resistance with dissimilar materials. J. Appl. Phys. 108, 044914 (2010).

Zhang, P., Lau, Y. Y. & Gilgenbach, R. M. Thin film contact resistance with dissimilar materials. J. Appl. Phys. 109, 124910 (2011).

Lam, Y. Z., Swingler, J. & McBride, J. W. The contact resistance force relationship of an intrinsically conducting polymer interface. IEEE Trans. Comp. Pack. Tech. 29, 294-302 (2006).

Liu, W., Menciassi, A., Scapellato, S., Dario, P. & Chen, Y. A biomimetic sensor for a crawling minirobot. Robot. Auton. Syst. 54, 513-528 (2006).

Oh, K. W., Park, H. J. & Kim, S. H. Electrical property and stability of electrochemically synthesized polypyrrole films. J. Appl. Polym. Sci. 91, 3659-3666 (2004).

Li, Y. et al. A flexible strain sensor from polypyrrole-coated fabrics. Synthetic Met. 155, 89-94 (2005). Abstract Only.

Jiang, M. J., Dang, Z. M. & Xu, H. P. Significant temperature and pressure sensitivities of electrical properties in chemically modified multiwall carbon nanotube/methylvinyl silicone rubber nanocomposites. Appl. Phys. Lett. 89, 182902 (2006). Abstract Only.

De la Vega, A., Sumfleth, J., Wittich, H. & Schulte, K. Time and temperature dependent piezoresistance of carbon nanofiller/polymer composites under dynamic load. J. Mater. Sci. 47, 2648-2657 (2012). Abstract Only.

Wu, J. Zhou, D., Too, C. O. &Wallace, G. G. Conducting polymer coated lycra. Synthetic Met. 155, 698-701 (2005). Abstract Only.

Ochoteco, E. et al. All-plastic distributed pressure sensors: taylor-made performance by electroactive materials design. Microsyst. Technol. 14, 1089-1097 (2008) Abstract Only.

Papakostas, Thomas V., Julian Lima, and Mark Lowe. "A large area force sensor for smart skin applications." Sensors, 2002. Proceedings of IEEE. vol. 2. IEEE, 2002.

King, M. G., et al. "Porous PDMS force sensitive resistors." Procedia Chemistry 1.1 (2009): 568-571.

Rizvi, Reza, and Hani Naguib. "Porosity and composition dependence on electrical and piezoresistive properties of thermoplastic polyurethane nanocomposites." Journal of Materials Research 28.17 (2013): 2415-2425.

Weiß, Karsten, and Heinz Worn. "The working principle of resistive tactile sensor cells." Mechatronics and Automation, 2005 IEEE International Conference. vol. 1. IEEE, 2005.

Kuang, Jun, et al. "A hierarchically structured graphene foam and its potential as a large-scale strain-gauge sensor." Nanoscale 5.24 (2013): 12171-12177.

Jackman, R. J., Duffy, D. C., Cherniavskaya, O. & Whitesides, G. M. "Using elastomeric membranes as dry resists and for dry lift-off". Langmuir 15, 2973-2984 (1999).

Tombler, T.W., et al. "Reversible electromechanical characteristics of carbon nanotubes under local-probe manipulation". Nature 405, 769-772 (2000).

Jones, J., Lacour, S. P., Wagner, S. & Suo, Z. G. "Stretchable wavy metal interconnects". J. Vac. Sci. Technol. A 22, 1723-1725 (2004).

Bekyarova, E. et al. "Electronic properties of single-walled carbon nanotube networks". J. Am. Chem. Soc 127, 5990-5995 (2005). Abstract Only.

Someya, T. et al. "Conformable, flexible, large-area networks of pressure and thermal sensors with organic transistor active matrixes". Proc. Natl Acad. Sci. USA 102, 12321-12325 (2005).

Nosho, Y., Ohno, Y., Kishimoto, S. & Mizutani, T. "The effects of chemical doping with F(4)TCNQ in carbon nanotube field-effect transistors studied by the transmission-line-model technique". Nanotechnology 18, 415202 (2007).

Khang, D. Y. et al. Molecular scale buckling mechanics in individual aligned single-wall carbon nanotubes on elastomeric substrates. Nano Lett. 8, 124-130 (2008).

LeMieux, M. C. & Bao, Z. N. "Flexible electronics: stretching our imagination". Nature Nanotech. 3, 585-586 (2008). Abstract Only.

Dickey, M. D. et al. "Eutectic gallium-indium (EGaIn): a liquid metal alloy for the formation of stable structures in microchannels at room temperature". Adv. Funct. Mater. 18, 1097-1104 (2008).

Ko, H. C. et al. "A hemispherical electronic eye camera based on compressible silicon optoelectronics". Nature 454, 748-753 (2008).

Cotton, D. P. J., Graz, I. M. & Lacour, S. P. "A multifunctional capacitive sensor for stretchable electronic skins". IEEE Sens. J. 9, 2008-2009 (2009).

Sekitani, T. et al. "Stretchable active-matrix organic light-emitting diode display using printable elastic conductors", Nature Mater. 8, 494-499 (2009).

Graz, I. M., Cotton, D. P. J. & Lacour, S. P. "Extended cyclic uniaxial loading of stretchable gold thin-films on elastomeric substrates". Appl. Phys. Lett. 98, 071902 (2009). Abstract Only.

Tahk, D., Lee, H. H. & Khang, D. Y. "Elastic moduli of organic electronic materials by the buckling method". Macromolecules 42, 7079-7083 (2009). Abstract Only.

Kim, K. S. et al. "Large-scale pattern growth of graphene films for stretchable transparent electrodes". Nature 457, 706-710 (2009).

Avouris, P. "Carbon nanotube electronics and photonics". Phys. Today 62,34-40 (2009).

Hu, L. B., Yuan, W., Brochu, P., Gruner, G. & Pei, Q. B. "Highly stretchable, conductive, and transparent nanotube thin films". Appl. Phys. Lett. 94, 161108 (2009). Abstract Only.

Yu, C. J., Masarapu, C., Rong, J. P., Wei, B. Q. & Jiang, H. Q. "Stretchable supercapacitors based on buckled single-walled carbon nanotube macrofilms", Adv. Mater. 21, 4793-4797 (2009).

Cao, Q. & Rogers, J. A. "Ultrathin films of single-walled carbon nanotubes for electronics and sensors: a review of fundamental and applied aspects". Adv. Mater. 21, 29-53 (2009).

So, J. H. et al. "Reversibly deformable and mechanically tunable fluidic antennas", Adv. Funct. Mater. 19, 3632-3637 (2009).

Roberts, M. E., Sokolov, A. N. & Bao, Z. N. "Material and device considerations for organic thin-film transistor sensors". J. Mater. Chem. 19, 3351-3363 (2009). Abstract Only.

Bae, S. et al. "Roll-to-roll production of 30-inch graphene films for transparent electrodes", Nature Nanotech. 5, 574-578 (2010).

Feng, C. et al. "Flexible, stretchable, transparent conducting films made from superaligned carbon nanotubes". Adv. Funct. Mater. 20, 885-891 (2010). Abstract Only.

Kim, B. Y. S., Rutka, J. T. & Chan, W. C. W. "Current concepts: nanomedicine". New Engl. J. Med. 363, 2434-2443 (2010).

(56) References Cited

OTHER PUBLICATIONS

Kim, D. H. et al. "Dissolvable films of silk fibroin for ultrathin conformal biointegrated electronics". Nature Mater. 9, 511-517 (2010).
Kim, R. H. et al. "Waterproof AlInGaP optoelectronics on stretchable substrates with applications in biomedicine and robotics". Nature Mater. 9, 929-937 (2010). Abstract Only.
Viventi, J. et al. "A conformal, bio-interfaced class of silicon electronics for mapping cardiac electrophysiology". Sci. Transl. Med. 2, 24ra22 (2010).
Zhang, Y. Y. et al. "Polymer-embedded carbon nanotube ribbons for stretchable conductors". Adv. Mater. 22, 3027-3031 (2010).
Hu, L. B., Hecht, D. S. & Gruner, G. "Carbon nanotube thin films: fabrication, properties, and applications". Chem. Rev. 110, 5790-5844 (2010). Book Table of Contents Only.
Kubo, M. et al. "Stretchable microfluidic radiofrequency antennas". Adv. Mater. 22, 2749-2752 (2010).
Chun, K. Y. et al. "Highly conductive, printable and stretchable composite films of carbon nanotubes and silver". Nature Nanotech. 5, 853-857 (2010).
Lipomi, D. J., Tee, B. C.-K., Vosgueritchian, M. & Bao, Z. N. "Stretchable organic solar cells". Adv. Mater. 23, 1771-1775 (2011). Abstract Only.

\* cited by examiner

SKIN-CONFORMAL SENSORS

RELATED DOCUMENTS

This patent document claims benefit under 35 U.S.C. § 119 of U.S. Provisional Patent Application Ser. No. 62/023,684, entitled "Skin-Conformal Sensors" and filed on Jul. 11, 2014, and with two Appendices; this provisional patent document and its appendices are fully incorporated herein by reference.

FEDERALLY-SPONSORED RESEARCH AND DEVELOPMENT

This invention was made with Government support under contract FA9550-12-1-0190 awarded by the Air Force Office of Scientific Research. The Government has certain rights in this invention.

OVERVIEW

Aspects of the present disclosure are believed to be applicable to a variety of different types of devices, systems and arrangements involving sensors and microstructures that interface with a subject. In certain embodiments, sensors are pressure sensors, and the device can be a wearable device for mobile healthcare systems. Additionally, the microstructures can include conductive, insulative, or semiconductive materials. The microstructures can provide contact between the electronic devices and human skin which can be important for skin-adaptability and detections of bio-signals that can provide clinically-valuable information. The microstructures can allow for conformability on non-flat surfaces, for the above described skin/healthcare and to other applications, and enhancement in the signal-to-noise ratio of the retrieved signals. Additionally, certain pressure sensors, consistent with various aspects of the present disclosure, are capable of measuring pulsations of internal jugular venous pulses stemming from a human neck. This capability allows for integration into a simple, portable transmitter and receiver, and can allow for expeditious diagnosis of cardiovascular and cardiac illnesses.

Various aspects of the present disclosure are directed toward a sensor device, in the form of apparatuses and methods, that includes an upper portion including a plurality of layers including at least one sensor (such as a pressure sensor), and a lower portion including a layer of microstructures. The microstructures can interface with skin of a subject and interlock the skin with the at least one sensor. Additionally, in certain embodiments, the microstructures and the at least one pressure sensor are configured to measure at least one of pulsations of venous pulses or arterial pulses of the subject, temperature of the subject, and electrocardiogram and/or electroencephalogram (EEG) of the subject. The skilled artisan would appreciate that the upper portion and lower portion refer to remote and skin-interfacing portions of the sensor device, respectively. Further, the microstructures can be configured to enhance the measurement of at least one of pressure pulses or waveforms that arise from venous pulses or arterial pulses of the subject, temperature of the subject, electrocardiogram and/or EEG parameters obtained from the subject, pulsations of venous pulses or arterial pulses of the subject, breathing, temperature of the subject, and electrocardiogram of the subject. Additionally, certain implementations of apparatuses and methods optionally include circuitry that collects pressure data from the at least one pressure sensor, and a wireless transmitter that transmits the pressure data to a remote device, and the microstructures include an adhesive portion to stick to the subject.

In certain other related embodiments, the upper portion includes another set of microstructures that are three-dimensional (e.g., pyramidal) in shape and have a height and width of less than 100 μm and are spaced apart by less than 100 μm. For example, in some aspects, the microstructures can have a height of 3 μm, a width of 6 μm, and are spaced apart by approximately 4 μm. Further, the upper portion can include another set of microstructures that are pyramids in shape, and the other set of microstructures form a dielectric layer.

Certain microstructures, consistent with the various aspects of the present disclosure, can be hair-like structures having various shapes and stiffness. The microstructures can be symmetric or asymmetric structures. Optionally, the microstructures can be configured to adhere to surfaces, and/or enhance adhesion to the subject. In certain more specific embodiments, the microstructures are of various shapes configured to enhance adhesion. Additionally, certain microstructures can include a flat region on top of a hair-like structure. The pressure sensors can also include resistive pressure sensors or capacitive pressure sensors. Further, the microstructures can be configured to enhance lateral force measurements of the subject, and the microstructures are configured and arranged to allow transduction of the lateral force. The microstructures can also enhance friction measurements of the subject. Further, the microstructures can be uniformly or non-uniformly distributed across the lower portion or of different heights.

DESCRIPTION OF THE FIGURES

Various example embodiments may be more completely understood in consideration of the following detailed description in connection with the accompanying drawings, in which.

Figure 1A:
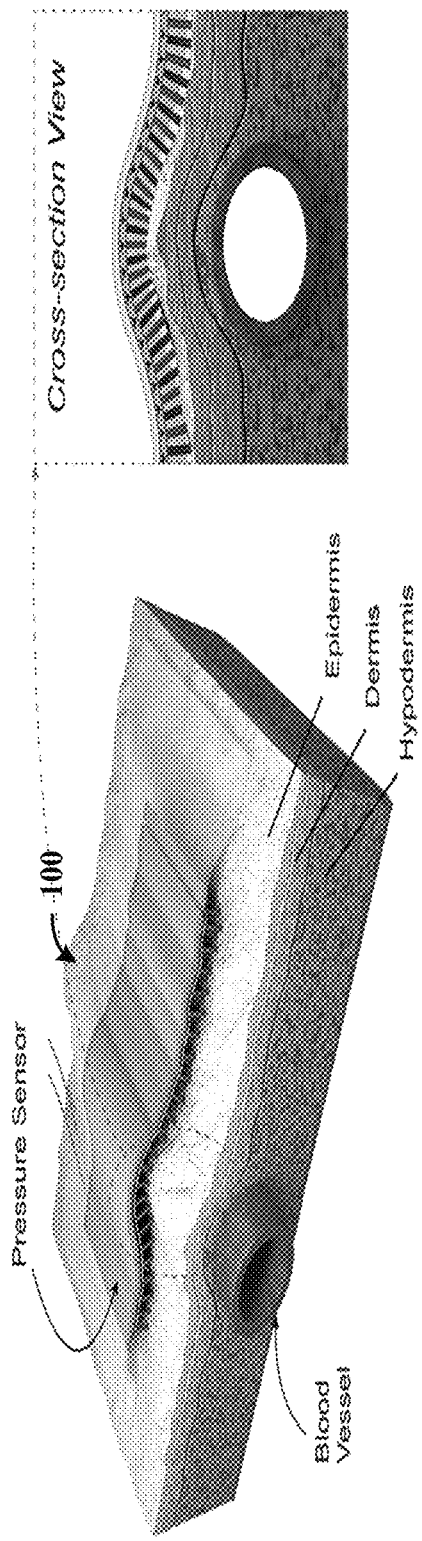
FIG. 1A shows a sensor device in accordance with various embodiments.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving sensors and microstructures to interface with skin of a subject. In certain implementations, aspects of the present disclosure have been shown to be particularly beneficial when used in the context of collecting physiological data from a subject using the sensors and microstructures, or with microstructures that are hair-like structures having various shapes and stiffness to enhance adhesion to the subject. While not necessarily so limited, various aspects may be appreciated through a discussion of examples using such exemplary contexts.

According to various example embodiments, aspects of the present disclosure are directed to a sensor device that can conform to the subject's skin to enhance adhesion and, thereby, increase accuracy in physiological data measured from the subject. The human body and/or other subject's skin consists of many non-flat surfaces and fine topology. This inconsistency in surfaces of the skin can make it difficult to create a conformal contact on the skin. Conformal skin contact between a sensor device and skin of a subject can be used for collecting physical data, e.g., pulsation, temperature, and electrocardiogram or electroencephalogram (EEG). Some conformal-contact devices can include the use of substrates for conformal contact with skin. For example, a sensitive pressure sensor and integrated-multifunctional device using a stretchable network can be used. Despite the performance and conformity of such devices, a skin-attachable device that is simple to fabricate and robust for practical remote diagnosis can present challenges to manufacture and/or materialize. For instance, the fabrication process is complicated and some of the materials involved are delicate.

Embodiments in accordance with the present disclosure can include use of manufactured microstructures on a sensor device. The microstructures can be hair-like structures with various shapes and stiffness. For example, the microstructures can be bio-inspired. In some instances, Gecko-inspired structures can be used as an effective interfacial skin-adhesive layer for electrocardiography (ECG) measurements and for drug-delivery systems. Other interesting interfacial systems of 'bio-mechanics' and 'mechano-transduction' can be found in nature, such as gears of insect legs, cerci of crickets for flow sensing, wing-locking structures of beetles, and cochlea in the inner ear, in which all of these examples involve 'microhair structures' to allow sensing and transferring of various mechanical forces.

The sensor devices can be formed of an upper portion containing at least one sensor and a lower portion that includes a layer of microstructures to interface with skin of the subject and interlock the skin with the at least one sensor. The sensor device can include flexible pressure sensors with signal amplification from the microstructures. For example, using a sensor device in accordance with the present disclosure can result in approximately twelve times enhancement in signal-to-noise ratio (SNR) via contact between the sensors and the irregular surface of the epidermis as compared to a sensor device that does not include microstructures. In addition, the microstructure layers, which can include polydimethysiloxane (PDMS) microhair-structured interfacial layers, can provide a non-invasive conformal attachment to the skin with biocompatibility.

For example, the microstructures can allow for conformability on non-flat surfaces and enhancement in the signal-to-noise ratio of the retrieved signals. In some embodiments this can be accomplished by incorporating biocompatible PDMS microstructures onto a pressure sensor fabricated on substrates. The microstructures allow for mechanical interlocking between the sensors and skin. For example, the microstructures can result in an approximate twelve times increase in the signal-to-noise ratio in the generated capacitive signals. Further, surprisingly, sensor devices in accordance with the present disclosure are capable of measuring pulsations of internal jugular venous pulses stemming from a human neck. This capability allows for integration of the sensor device into a portable transmitter and receiver, and can allow for expeditious diagnosis of cardiovascular and cardiac illnesses.

In various embodiments, the sensor device optionally includes circuitry including a wireless transmitter. A sensor device with a wireless transmitter is capable of measuring signals from the deep-lying internal jugular venous pulses (JVPs). The unique waveforms of the JVPs can include clinical information that may be used for preliminary diagnosis of heart failure. For example, the JVP waveform can be associated with diagnostic and pathognomic of clinical conditions such as arrhythmias, right heart hemodynamics, or pericardial disease. Further, elevated JVP in patients with heart failure can be associated with increased risk of hospitalization for heart failure and/or hospital admission death. Almost one out of every three deaths results from cardiovascular disease. However, the absolute JVP pressure and/or signals can be difficult to measure. Although several pressure sensors have been reported for measuring radial artery wave forms, more clinical values for heart disease diagnosis have been realized with detection of the deep lying JVP and its waveform. Traditionally, JVP is detected by visual inspection, or non-invasive crystal microphone, cardiac MRI, or echocardiography. However, such traditional detection can be error-prone, time-delayed, complicated, and/or expensive. Real-time monitoring of JVP waveforms can provide valuable information for initial screening to people suffering from heart diseases or recovering from a heart surgery. Sensor devices, in accordance with the present disclosure, can be used for real-time monitoring of JVP.

Turning now to the figures, FIG. 1A shows an example sensor device 100 in accordance with various embodiments. The sensor device 100, in various embodiments, can be a fabricated sensor that can be used as a wearable electronic to monitor arterial tonometry or pulses in the neck (e.g., the waveforms of JVPs from the epidermis above subcutaneous vein). For example, the sensor device can be used to obtain valuable information related to cardiovascular diseases.

The sensor device 100 can include an upper portion and a lower portion. In various embodiments, the upper portion includes a plurality of layers including at least one sensor. The at least one sensor can include at least one pressure sensor. The pressure sensors can be resistive pressure sensors and/or capacitive pressure sensors.

The lower portion includes a layer of microstructures. The microstructures, sometimes herein referred to as "microhairs", can include hair-like structures. The microstructures can interface with skin of a subject and interlock the skin with the at least one sensor. In various embodiments, the microstructures can adhere to surfaces, such as enhancing adhesion to the subject. The subject can include a patient, a human, an animal, and a moving object, among other subjects. For example, the microstructures can include an adhesive portion to stick to the subject.

The sensor and microstructures can be used to measure a variety of physiological signals. For example, the physiological signals can include pulsations of venous pulse or arterial pulses of the subject, temperature of the subject, and electrocardiogram and/or electroencephalogram (EEG) of the subject. The microstructures, in various embodiments, can increase the contact between the skin and the at least one sensor as compared to a sensor device without the microstructures. For example, the microstructures can enhance measurements, such as pressure pulses or waveforms that arise from venous pulses or arterial pulses of the subject, temperature of the subject, and electrocardiogram and/or EEF parameters obtained from the subject. The enhancement, in some embodiments can include an enhanced lateral force measurement of the subject. For example, the microstructures can allow for transduction of the lateral force. Alternatively and/or in addition, the microstructures can enhance friction measurements of the subject.

In accordance with various embodiments, the sensor device 100 can include circuitry configured to collect pressure data from the at least one pressure sensor. Further, the sensor device can include a wireless transmitter to transmit the pressure data collected to a remote device.

Figure 1B:
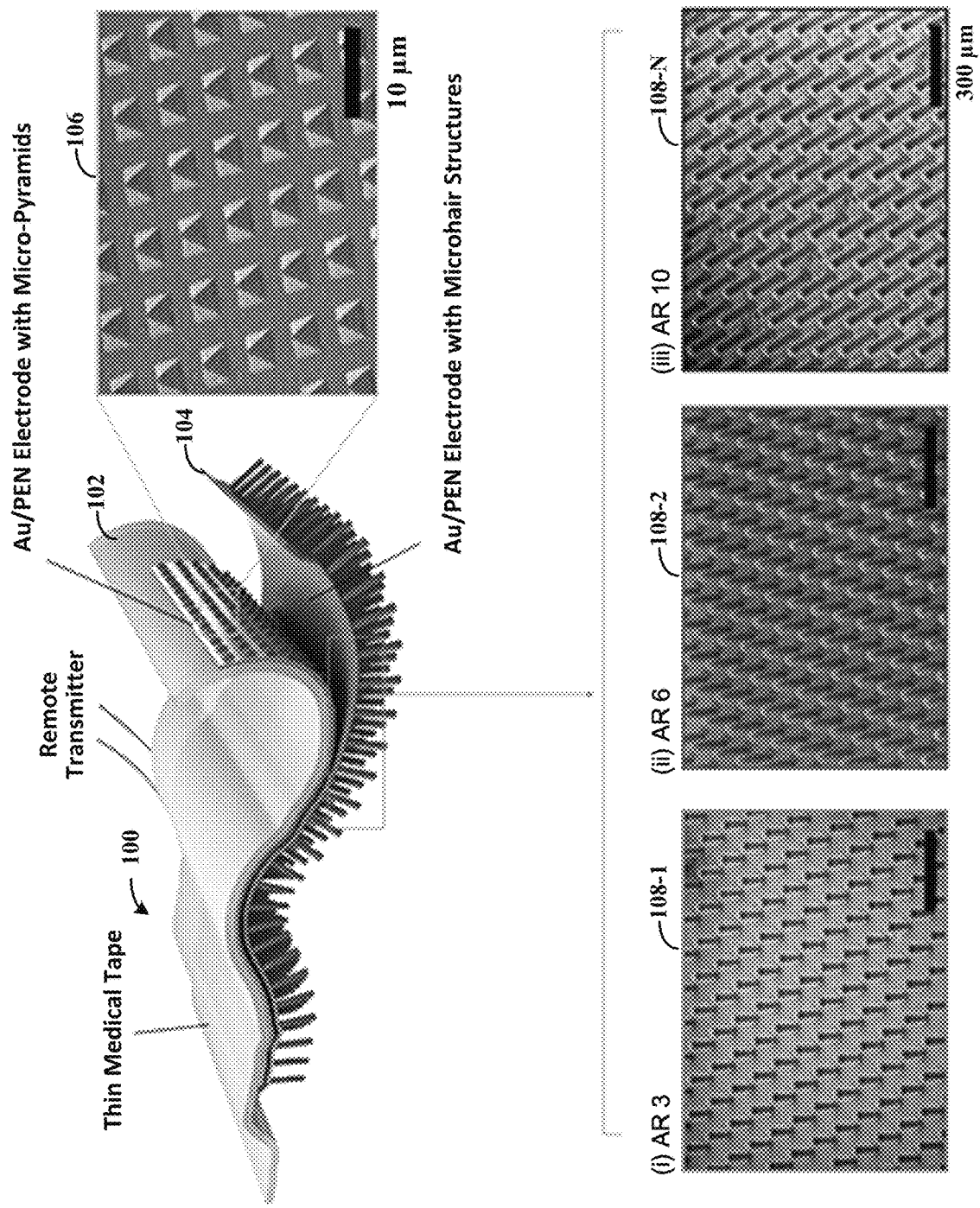
FIG. 1B shows a sensor device with microstructures on a lower portion of the sensor device in accordance with various embodiments.

As illustrated by FIG. 1B, in some embodiments the microstructures 108-1, 108-2 . . . 108-N (herein generally referred to as "microstructures 108" for ease of reference) can be a variety of shapes. For example, the hair-like structures can have various shapes and stiffness. The shapes, in some embodiments, can enhance adhesion to the subject. For example, the microstructures 108 can be symmetric and/or asymmetric in shape and can include conductive, insulative, or semiconductive materials.

The microstructures 108 can be distributed on the lower portion 104 in a variety of manners. For example, the microstructures 108 can be uniformly distributed, non-uniformly distributed, and/or have varying heights.

In a number of embodiments, the upper portion 102 of the sensor device 100 optionally include another set of microstructures 106. The other set of microstructures 106 can be pyramids in shape. For example, the other set of microstructures 106 can have a height and width of less than 100 µm and are spaced apart by less than 100 µm. For example, in some aspects, the other set of microstructures 106 can have a height of 3 µm, a width of 6 µm, and are spaced apart by approximately 4 µm. The other set of microstructures 106 can form a dielectric layer, or a conductive layer.

As illustrated by FIGS. 1A and 1B, the sensor device 100 can include a bandage-like electrical pressure sensor containing microstructures 108 (e.g., microhair structures) having various aspect ratios (ARs) (where: AR=l/2R, where l is the height and R is radius of microhair structures). For example, the sensor device 100 can be divided into two parts. First, the upper portion 102 of the sensor device 100, in some embodiments, is comprised of five consecutive layers of a polyethylene naphthalene (PEN) thin foil (12 µm), a chromium (Cr, 4 nm)/gold (Au) electrode layer (50 nm), a polyvinyl alcohol (PVA) adhesion layer (20 nm), followed by a pyramidal-shaped PDMS layer (e.g., the other set of microstructures 106, 6 µm in width, 3 µm in height, and a spacing of 3.8 µm). For example, such a microstructured dielectric layer can allow for enhanced sensitivity, reduced hysteresis and for full-stretchable devices. Such a concept can be applied to resistive pressure sensors. In addition, the thin PEN substrate and PDMS can allow for flexibility and biomedical compliance with the surface of the subject (e.g., human skin).

Second, the lower portion 104 of the sensor device 100 can contain laminated microstructures 108 (e.g., microhair structures, 30 µm in diameter, and different heights with AR of 3, 6, and 10) on the PVA side of the Au/Cr/PEN/PVA stack. The two halves 102, 104 can be laminated together with the Au on the lower portion 104 in contact with the PDMS 106 on the upper portion 102 and sealed using medical tape. In some examples, the medical tape can have a thickness of 18 µm. The medical tape allows for uniform adhesion of the capacitive active layer and enhancing the sensor's stability upon bending or deforming (such as the bending illustrated by FIG. 1B).

Figure 1C:
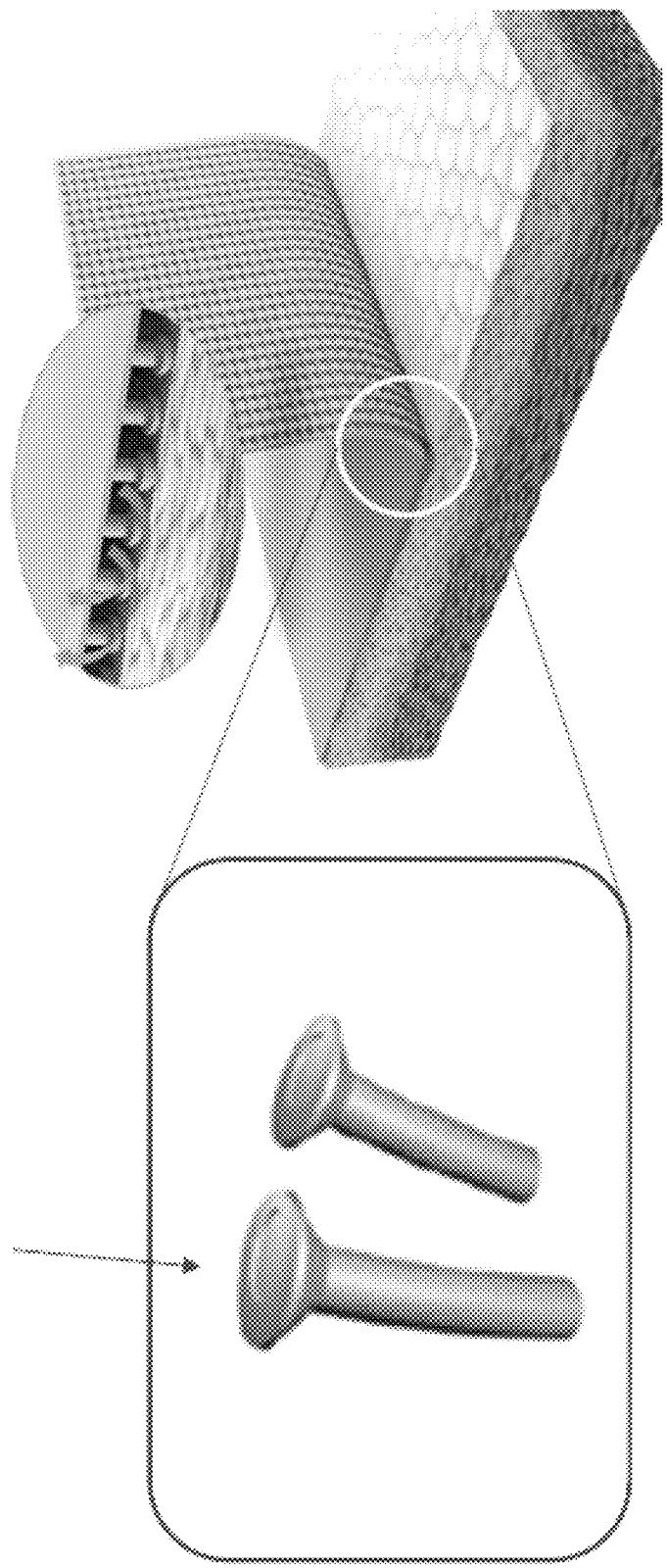
FIG. 1C shows an example of microstructures on a lower portion of a sensor device in accordance with various embodiments.

FIG. 1C shows an example of microstructures on a lower portion of a sensor device in accordance with various embodiments. In some embodiments, the surface of the microstructures configured to interface with a surface of the subject's skin can include a variety of shapes. For example, as illustrated by FIG. 1C, the microstructures can include a flat disc-like shape on the surface of the microstructures configured to interface with the surface of the subject's skin. In some instances, a porous film can be on the tip of the microstructures to form the flat disc-like shape.

In addition, the various embodiments described herein may be combined in certain embodiments, and various aspects of individual embodiments may be implemented as separate embodiments. For instance, aspects of FIG. 1A and/or FIG. 1B can be used to perform aspects of FIG. 2. Further, the sensor devices illustrated by FIGS. 1A-1B can be used to obtain the various results illustrated by FIGS. 3-6. And, in various aspects, the microstructures can include a variety of shapes and/or sizes.

Figure 2:
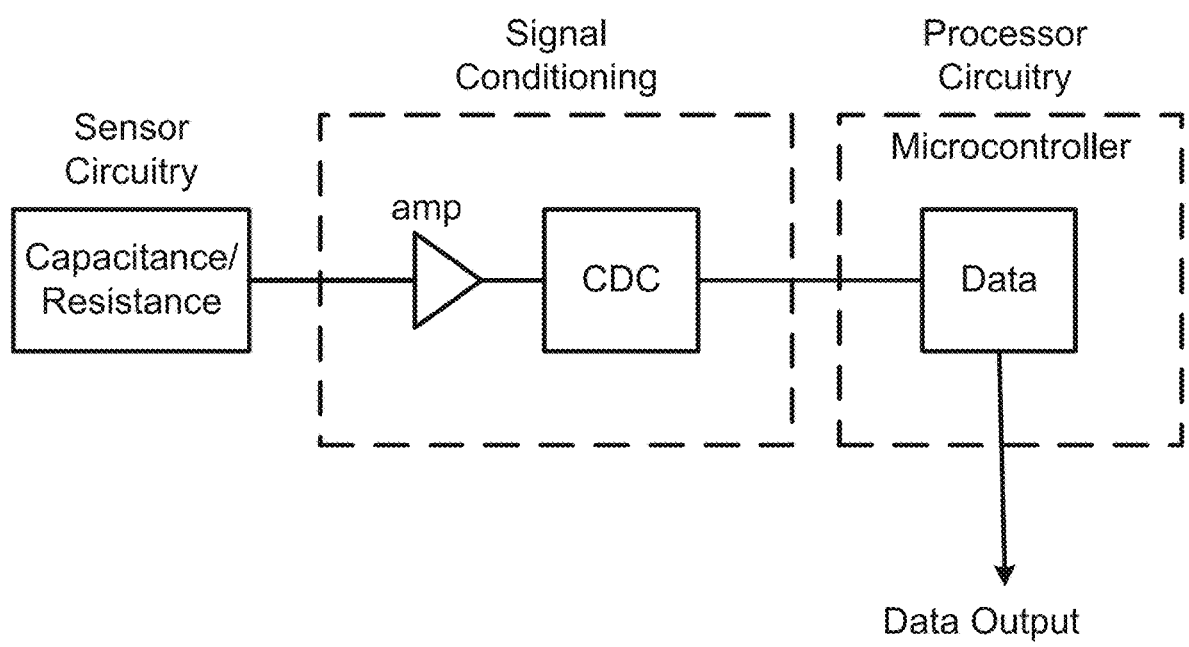
FIG. 2 shows example circuitry of a sensor device used to collect physiological signals in accordance with various embodiments of the present disclosure.

FIG. 2 shows example circuitry of a sensor device used to collect physiological signals in accordance with various embodiments of the present disclosure. As shown in FIG. 2, a capacitance and/or resistance is measured by sensor circuitry and the microstructures of the sensor device. The sensor circuitry, in various embodiments, can include at least one resistive pressure sensor and/or at least one capacitive pressure sensor. The capacitance and/or resistance (e.g., physiological signals) measured by the sensor circuitry and microstructures (e.g., microhair structures) can optionally be conditioned, in various embodiments. The signal conditioning can include amplification, filtering, and/or digital conversion, among other conditioning. For example, the signals measured by the sensor circuitry and indicative of the capacitance and/or resistance can be amplified, such as by the amplifier illustrated in FIG. 2. Sensors, that include a top electrode and bottom electrode, measure a physiological response (e.g., a physiological signal) based on a capacitance (and/or resistance) change. The amplified signals can be converted, in various embodiments, to a digital signal. As a specific example, to determine the change in capacitance and/or resistance as a function of the applied pressure, a capacitance to digital converter (CDC) circuit interfaces with the sensor (e.g., sensor circuitry), collects the capacitance and/or resistance signals (e.g., readings/measurements by the sensor circuitry), and converts the capacitance and/or resistance signals to digital signals.

A processor circuitry, such as a microcontroller circuit and/or a digital signal processor (DSP), is programmed to control the CDC circuit and read sensor data (e.g., at a rate of 90 Hertz (Hz)) in a digital form. For example, the processor circuitry can receive the measured signals (e.g., from the CDC) and determine a change in capacitance and/or resistance. The change can be determined using two or more signals. Although the example circuitry of FIG. 2 illustrates the signals being converted to digital form, embodiments in accordance with the present disclosure are not so limited. For example, the microcontroller can process signals in digital and/or analog form. For further information regarding various sensors including, e.g., pressure sensors, reference may be made to U.S. Pat. Nos. 8,764,670 and 8,764,668, which are incorporated herein by reference for the specific and general teachings of sensing arrangements.

Additionally, depending on the physiological signals that are measured, the capacitive and/or resistive change is correlated with a physiological response, and the data is output by the processor circuitry. This sensor data can be wirelessly transmitted to a remote device (e.g., a computer), which can be visually displayed.

Experimental Results

In a number of embodiments, various microhairs with different ARs and rigidity can be designed. These designs include sensors with flat bottom layers (AR=0) and microhair-structured sensors with ARs of 3, 6, and 10. The microhairs can be 30 μm in diameter and arranged in hexagonal arrays, along with a spacing ratio ($\delta_s$) of 3 ($\delta_s = l_s/2R$, where $l_s$ is the gap between hairs and R is radius of hairs), as shown in FIG. 1B.

FIGS. 3A-3D show radial artery pulse waves and characterization of the capacitive response, in accordance with various embodiments. Radial artery pulse waves can be measured using four different types of sensor devices and the collected data can be plotted, as illustrated in these figures. The four different sensor devices can include distinct geometries including a first sensor device with a flat PEN surface (e.g., illustrated by FIG. 3A), a second sensor device with PDMS microhair structures with AR 3 (e.g., illustrated by FIG. 3B), a third sensor device with PDMS microhair structures with AR 6 (e.g., illustrated by FIG. 3C), and a fourth sensor device with PDMS microhair structures with AR 10 (e.g., illustrated by FIG. 3D). The pulse data can be measured from an identical contact spot, as denoted with an arrow in the inset images of FIGS. 3A and 3B. This can minimize the variance between the signal retrieval from the four distinct sensors. The pulsations of the radial artery can be monitored using a wireless measurement system, which is comprised of a computer-based user interface via an RF Modules (XBEE2) and a wireless transmitter. The magnitudes of the retrieved pulse waveforms can be amplified upon increasing the AR of the microhair structures (FIG. 3A-D). For example, the right inset of the FIGS. 3A-3D illustrates the sensitivities of the different sensor devices, as measured by a function of the capacitance and/or resistance change over applied pressure. Surprisingly, approximately 12 times increase in the signal-to-noise ratio (SNR) can be observed when the pulse was measured using AR 10 microhair sensor (~32.42) as compared to the measurement with a flat device (~2.67). SNR can be calculated using the following equation:

$$SNR = avg(\Delta C_{max}/\sigma_{baseline},$$

where $avg(\Delta C_{max})$ is the average capacitance and/or resistance change of the maximum radial pulse, and $\sigma_{baseline}$ is the standard deviation of the baseline. The sensitivity (S) obtained using a force gauge with a pressure-sensitive pad (64 mm$^2$) can remain unchanged for all sensor devices and can be calculated to be around 0.55-0.58 kPa$^{-1}$ (FIG. 3A-D).

Figure 3A:
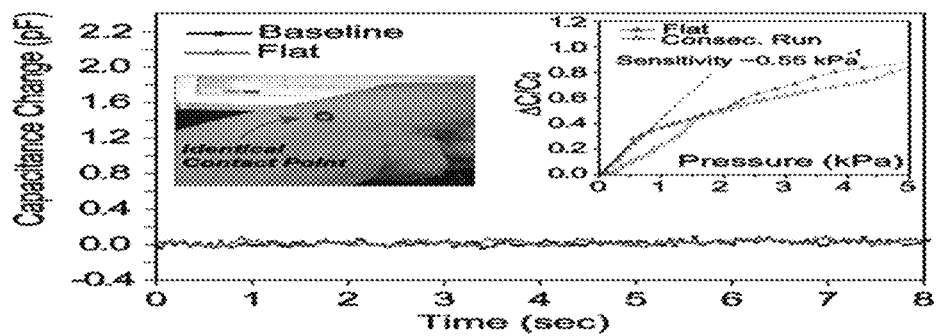
FIGS. 3A-F show examples of radial artery pulse waves and characterizations of the capacitive response, in accordance with various embodiments.
Figure 3B:
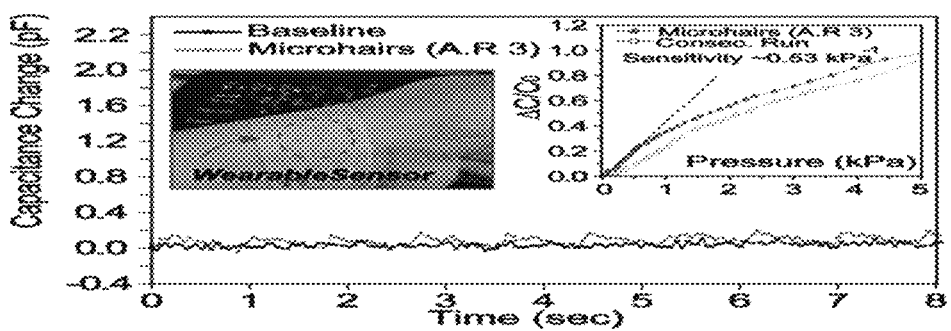
Figure 3C:
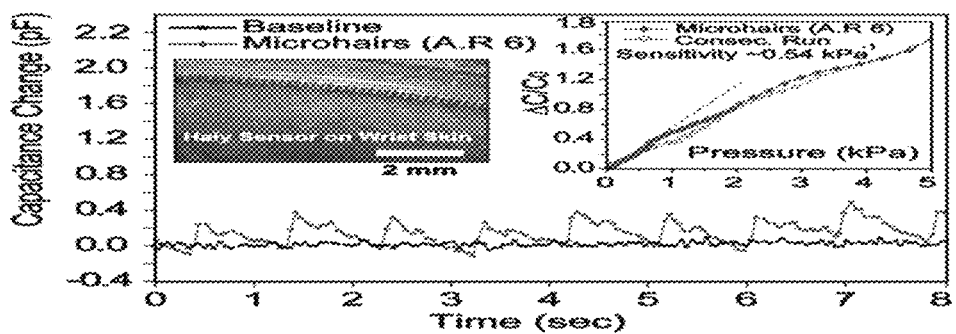
Figure 3D:
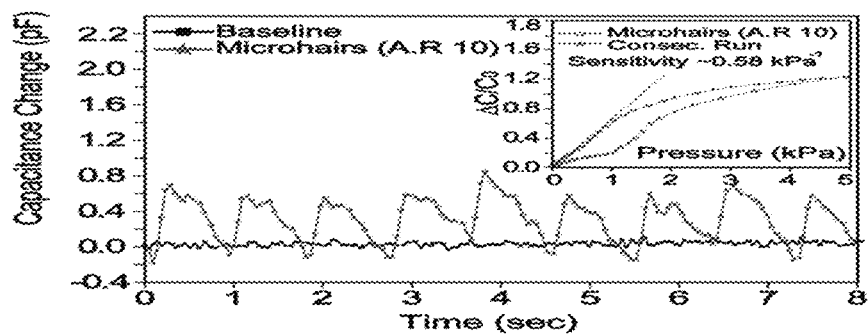

A slight decrease in the sensitivity and a larger hysteresis may be observed when using a sensor with high AR microhairs (AR=10, as illustrated by FIG. 3D), which can be mainly due to the slower recovery time of high AR elastic microhairs that are more susceptible to collapse upon higher pressure levels as compared to those of lower AR microhairs. Nonetheless, the sensitivities of the four sensors with different hair geometries can exhibit similar values. This can be attributed to the fact that sensitivity is a measurement dependent on the rate of change of the applied pressure, while the magnitude of the waveforms of the radial artery pressure is affected by the effective contact area between the sensor devices and the surface of skin above the subcutaneous artery. The sensitivity can be defined as the slope of the pressure-response curve:

$$S = \delta(\Delta C/C_0)/\delta p = (1/C_0) \cdot \delta C/\delta p,$$

where p denotes the applied pressure, and C and $C_0$ denote the capacitances (and/or resistances) with and without the applied pressure, respectively. In the case of radial artery pulse wave represented by the change in capacitance ($\Delta C$), the interpreted signals can be dominated by the ratio of the effective contact area ($A_{eff}$) between the sensors and the contacted skin right above the subcutaneous artery and the actual area of the fabricated devices ($A_0$), as represented by the equation:

$$\Delta C = C_0 \cdot S \cdot P_{physical}(A_{eff}/A_0),$$

where $P_{physical}$ is the continuing pressure arising from the human body such as the carotid pulse (approximate $\Delta 130$ millimeter of mercury (mmHg)), radial artery pulse (approximate $\Delta 35$ mmHg), or JVPs (approximate $\Delta 15$ mmHg).

Figure 3E:
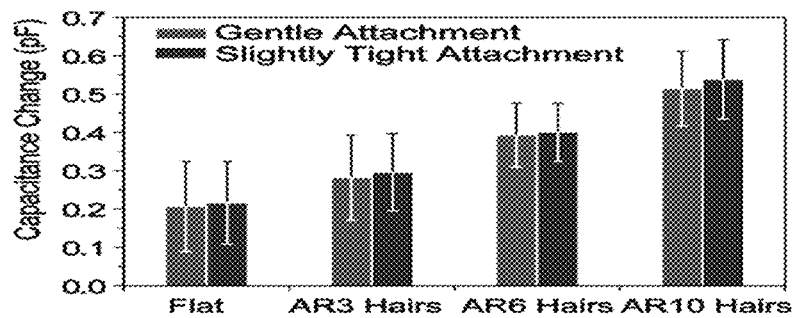

The validity of the obtained trend using sensors with four different geometries of microhairs (from flat to ARs of 3, 6, and 10) can be verified through statistical analysis of the capacitance and/or resistance change obtained from the artery pulse. FIG. 3E represents the average capacitance change that can be obtained respective to the artery pulse from the four different types of sensor devices. That is, FIG. 3E shows statistical data of the capacitive changes by applying different amounts of shear forces (<0.63N/cm$^2$) to the different sensor devices. The error bars represent the standard deviations. For example, data can be measured using 16 devices (four for each type) and averaged after performing measurements five times for each single device by removing and reattaching for each measurement. The trend is in agreement with those of FIG. 3A-D. For example, a slightly larger capacitive change (average 1.6%) can be added to the signal when the device is attached with applied shear force of 0.63 N/cm$^2$. In addition, two separate modes can be used for measuring the radial artery pulse using different amounts of loads (1 & 2 kilopascal (kPa), respectively) when attaching the microhair-structured sensors to the skin. A slightly larger capacitive change can be obtained when the load is 2 kPa, which can be attributed to the conformal contact of the microstructures to the skin as a result of the increased compressive force.

Figure 3F:
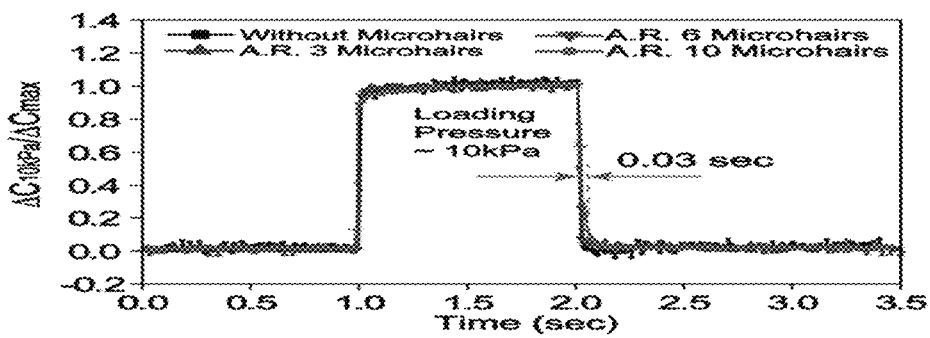

FIG. 3F shows the response and relaxation times of the capacitive pressure sensors with the step stimuli of loading and unloading 10 kPa for 2 seconds. The sensor devices can illustrate immediate response with an applied pressure, and using sensor devices that include PDMS micro-pyramid and an air-gap with dielectric constants ($\varepsilon_{air}$~1.0 and $\varepsilon_{PDMS}$~3.0). A delay (<0.03 seconds) may be observed for the device with a high AR microhair structures (AR 10) due to the elasticity of PDMS microhairs. However, the pressure sensing capability may not be affected, as the sensor devices can illustrate stability after a cycling test (comprised of loading and unloading of applied pressure at 10 kPa for 1 second and up to >3,000 times), maintaining the sensitivity of ~0.56 kPa$^{-1}$ and accurately detecting capacitance change of arterial pressure (~0.45 pF) without affecting the microhair structure arrays.

Figure 4A:
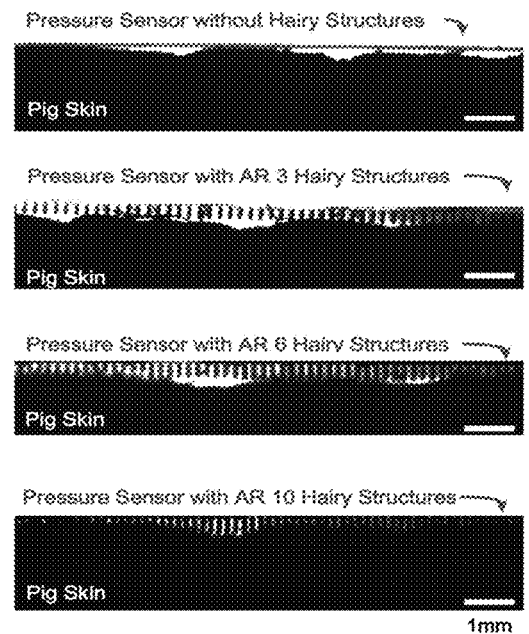
FIGS. 4A-4C show examples of cross-sectional profiles of the sensor devices with different geometries of microstructures in accordance with various embodiments.
Figure 4B:
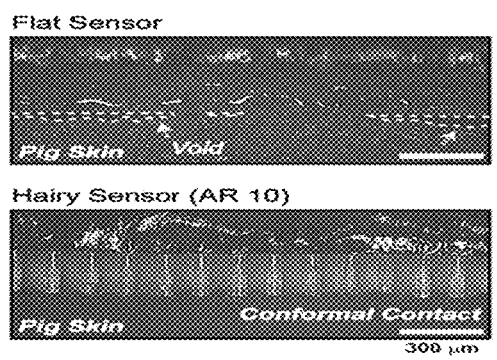
Figure 4C:
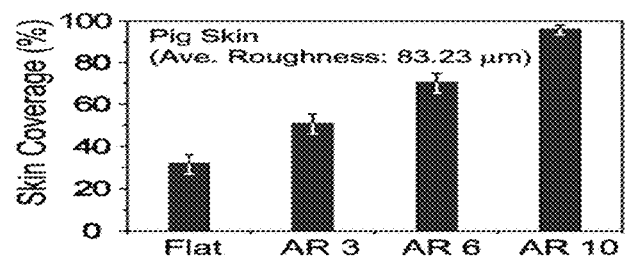

FIG. 4A shows cross-sectional profiles of the fabricated sensors with different geometries of microstructures (flat surface of PEN and 30 µm diameter micropillar arrays of PDMS with AR 3, 6, and 10), which can be used to estimate the effective contact area between the sensors and the skin of subject, such as a pig. The cross-sectional images can be taken by fixing the sensors and pig skin onto a sample holder, and mounting the sample holder onto a perpendicularly controllable stage with a force sensor. A load of approximately 1 kPa can be applied to the sensor to visualize the contact between the microhair structures and the skin. From the images of capacitive pressure sensors with flat geometry and microhair structures with (low) ARs of 3 and 6, both macro- and micro-sized voids can be observed between the sensors and the skin. These voids can prevent optimal contact of the effective area ($A_{eff}$) in between the devices and the skin. To better contrast the difference in the $A_{eff}$ with and without using the (high) AR microhair structures of 10 in a capacitive sensor system, magnified cross-section images of the interface between the fabricated sensors and hierarchically rough surface of skin can be taken, as displayed in FIG. 4B. Whereas the sensor with AR 10 microhair structures can contact the skin with conformity, micro-scale voids can be prevalent for the case of the flat sensor. Further, the percentage of skin coverage can be estimated by quantifying the black and white pixels of the optical images shown in FIG. 4A, and the results can include: flat (approximately 25%), AR 3 (approximately 52%), AR 6 (approximately 72%), and AR 10 (approximately 98%), as illustrated by FIG. 4C.

In addition to the cross-sectional analysis, the structural properties of skin can be investigated using atomic force microscopy (AFM) and optical microscopy. In general, skin can have a morphologically dual-level rough surface with micro and nano levels. The roughness of the examined skin, such as pig skin, can range from a minimum 1.9 nm to a maximum of 90 µm to 240 µm (average roughness approximately 18 µm, moisture-dependent) (via both AFM and optical microscopy). The detection of bio-pulsations can be due to microscale contractions and expansion of the skin, such that nanoscale roughness of the skin is rendered negligible. In some instances, such as with the pig skin, the microhair-structured arrays with AR of 10 (height=300 µm) may provide full coverage on the macroscopically rough surface of the skin via mechanical interlocking (load of approximately 1 kPa) as illustrated in FIGS. 4A and 4B, consequently leading to an optimal $A_{eff}$ for amplified capacitive signals.

Figure 5A:
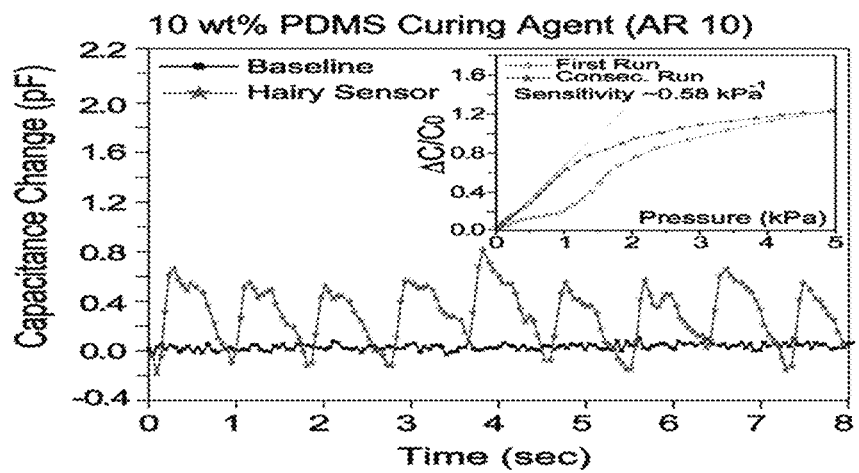
FIGS. 5A-5E show representations of pressure-response curves of radial artery pulse using different weight percent of a PDMS curing agent in accordance with various embodiments.
Figure 5B:
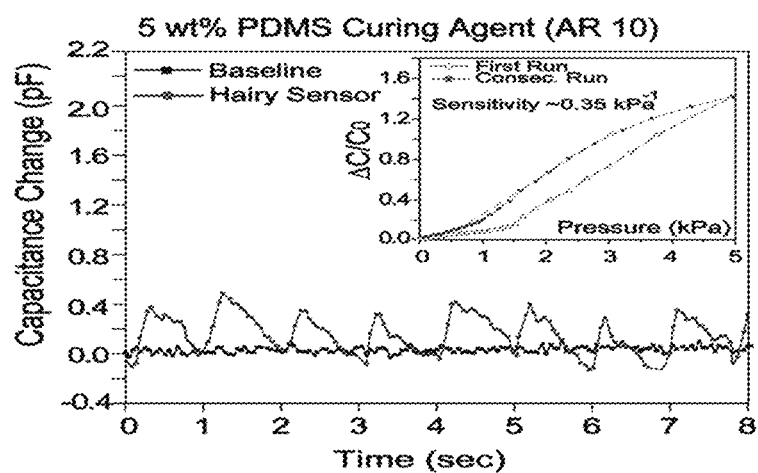
Figure 5C:
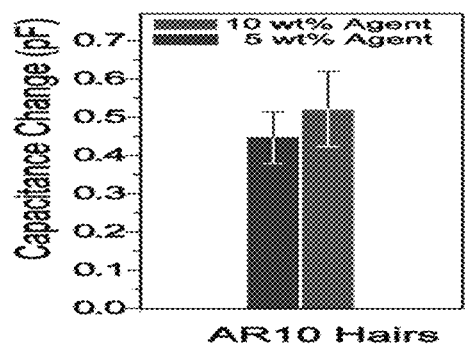
Figure 5D:
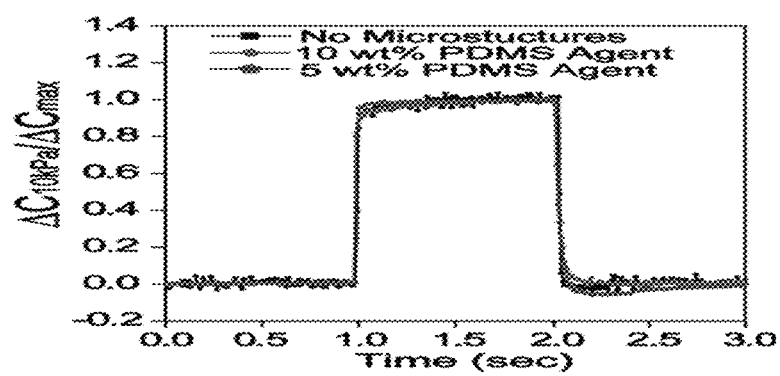

FIGS. 5A-5E show representations of pressure-response curves of radial artery pulse using different weight percent (wt %) of a PDMS curing agent. The effect of microhair structure's rigidity toward the sensitivity of the capacitive pressure sensors can also be investigated. The same geometry of microstructures (with AR 10) can again be used, while varying the elastic modulus (E). In specific, two sets of devices (4 for each set for statistical analysis) can be fabricated by varying the mixing ratio of the curing agent for the PDMS microhair structures. For the first set of devices, 10 wt % of curing agent can be used ($E_{10wt\%}$ approximately 1.9 MPa, e.g., hard microhair structures); while for the second set of devices, 5 wt % of curing agent can be used ($E_{5wt\%}$ approximately 0.4 megapascal (MPa), e.g., soft microhair structures). FIGS. 5A and 5B represent the pressure-response curves of radial artery pulse using 10 wt % and 5 wt % PDMS curing agent, respectively. The sensors can be measured using the same method as shown in FIG. 3. From FIG. 5A-C, it can be observed that the pulse waves retrieved from the soft microhair devices have a smaller capacitive change than those of the hard microhair devices, with an approximate 20% decrease in capacitance change. Surprisingly, the soft microhair devices can exhibit relatively low sensitivity (approximately 0.35 kPa$^{-1}$) as compared to that of the hard microhair devices (0.55-0.58 kPa$^{-1}$) in FIGS. 3 and 5A. Furthermore, the devices with different geometries can exhibit similar sensitivities, despite a noticeable gap in the magnitude of capacitance changes (a detailed reasoning for this unusual behavior is also addressed further herein). FIG. 5D shows the response and relaxation times of the three sets of microhair devices by applying a step stimuli through subsequent loading and unloading of an applied pressure of 10 kPa for 2 seconds. For the soft microhair pressure sensor, a negative change in capacitance can be observed during the measurement of the relaxation and steady-state (<0.3 seconds), which can be attributed to the viscoelastic behavior of the soft microhair structures.

Figure 5E:
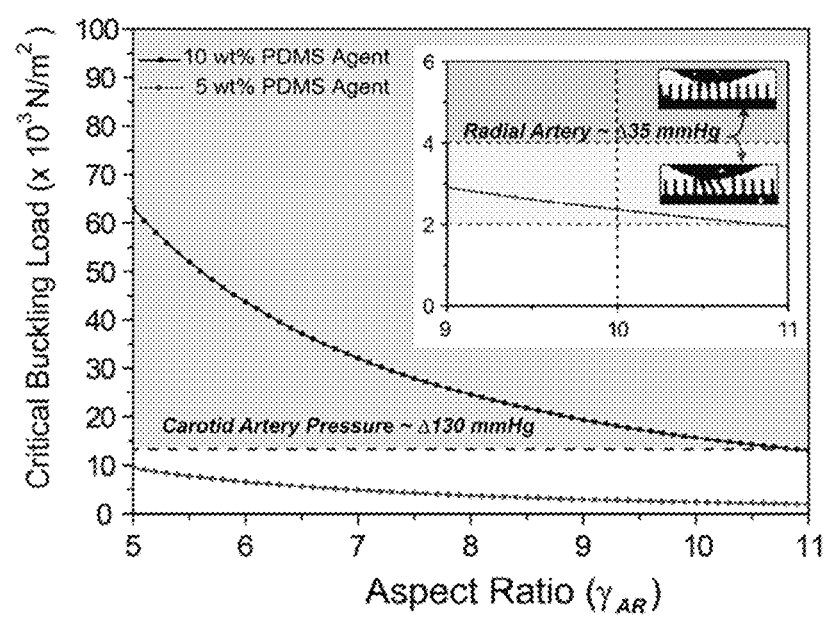

The surprising discrepancy in the sensitivities exhibited between the soft and hard microhair-structured pressure sensors, as based on two different mixing ratios of PDMS curing agent (5 and 10 wt %), can be explained by a mechanical analysis of buckling generation in the microhair arrays with an AR of 10. The buckling load ($P_{cr}$) that a microhair structure can withstand can be expressed as a relationship of geometrical and material properties:

$$P_{cr}=(\pi^2 \cdot E \cdot I)/16\gamma_{AR}^2,$$

where I is the moment of inertia (I=π·R/4), R is the radius, and $\gamma_{AR}$ is the AR of the microhair structures. As shown in FIG. 5E, the soft microhairs can buckle when an average radial artery force of approximately Δ35 mmHg (~4 kPa) is applied, whereas the rigid microhair structures can endure the compressive stress from a physical force of approximately 4 kPa. A model can provide the lower limitation of elastic modulus, orchestrated with the geometric features of height and diameter of the microstructures having a non-sticky property. The model can generate a simple guideline for the microhair-structured array on the pressure sensor to maximize their sensitivity. Further, the maximum elastic modulus ($E_{max}$<200 MPa) of the microhair-structured array is limited by the material's properties (i.e., of PEN substrate) for conferring flexibility with less-intrusive and more conformal attachment to skin, and can again be estimated using the model of Johnson, Kendall, and Roberts (JKR model) for the peeling strength. For general and specific information on the JKR model, reference is made to Kendall, K, Thin-film peeling—elastic term. J. Phys. D. Appl. Phys. 8, 1449-1452 (1975), which is fully incorporated herein by reference.

Figure 6A:
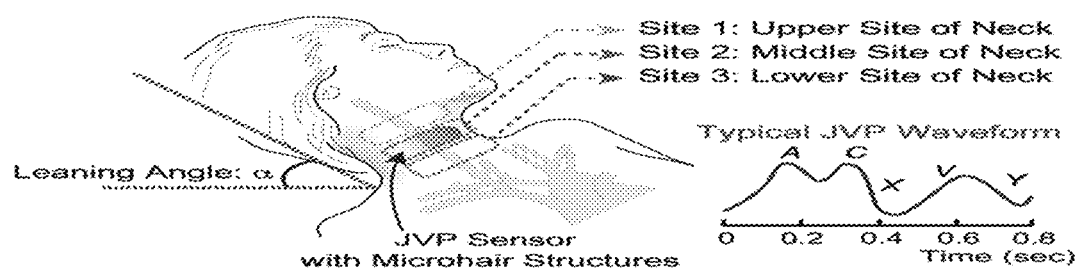
FIGS. 6A-6G show neck anatomy and measurements of pulses on contact sites of a neck of a subject with varying effective leaning angles in accordance with various embodiments.
Figure 6B:
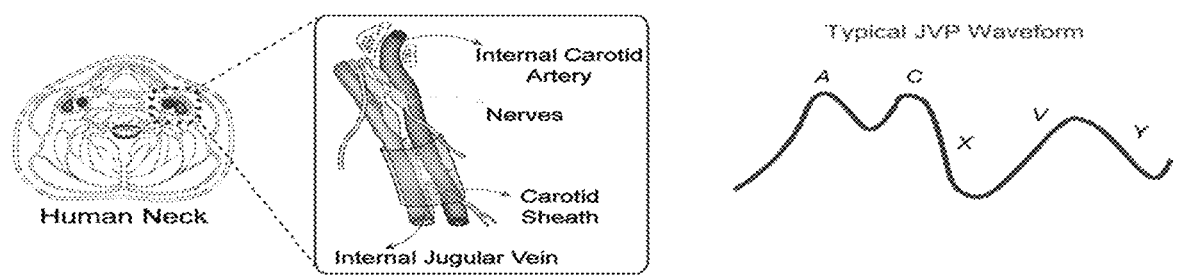
Figure 6C:
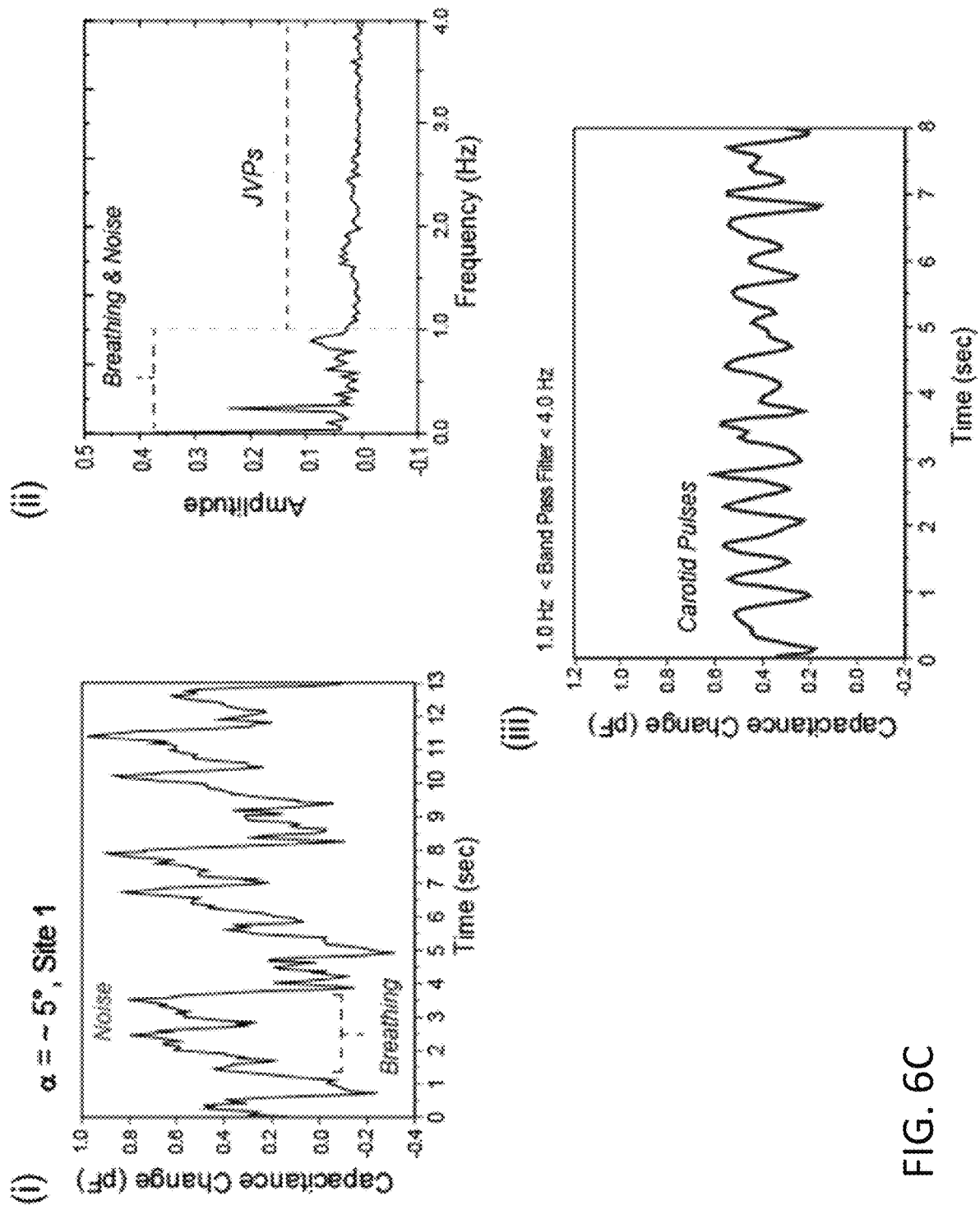
Figure 6D:
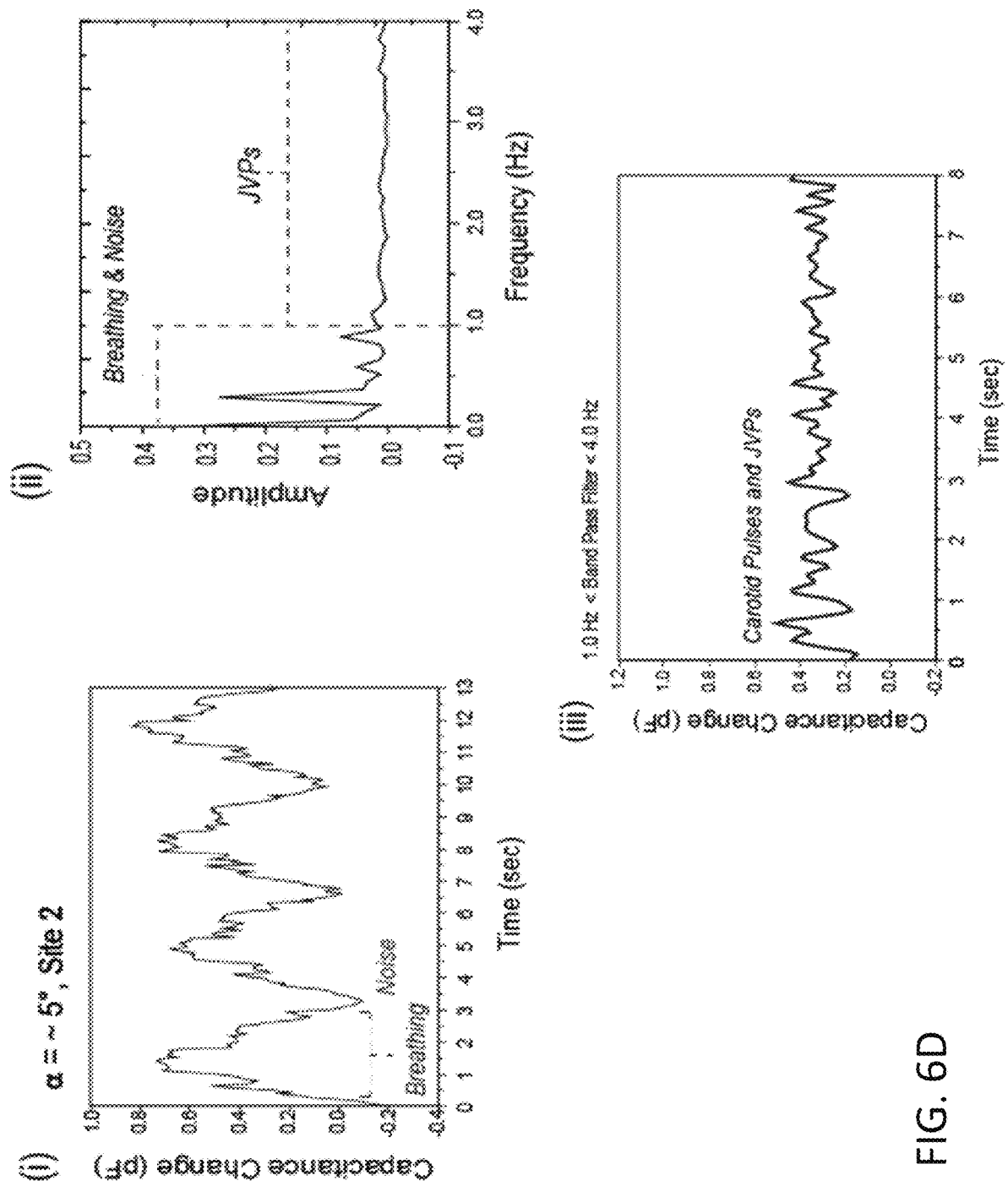
Figure 6E:
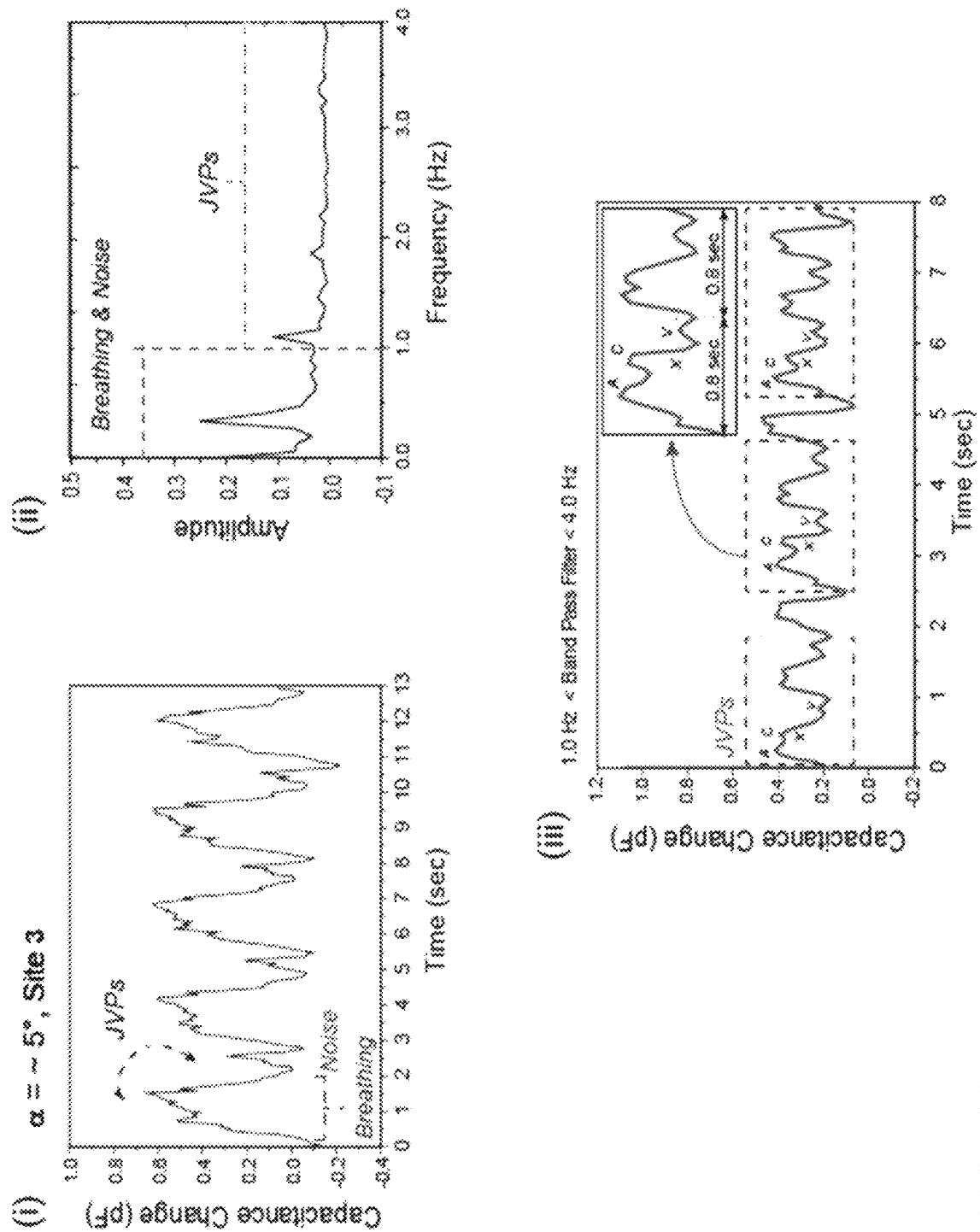
Figure 6F:
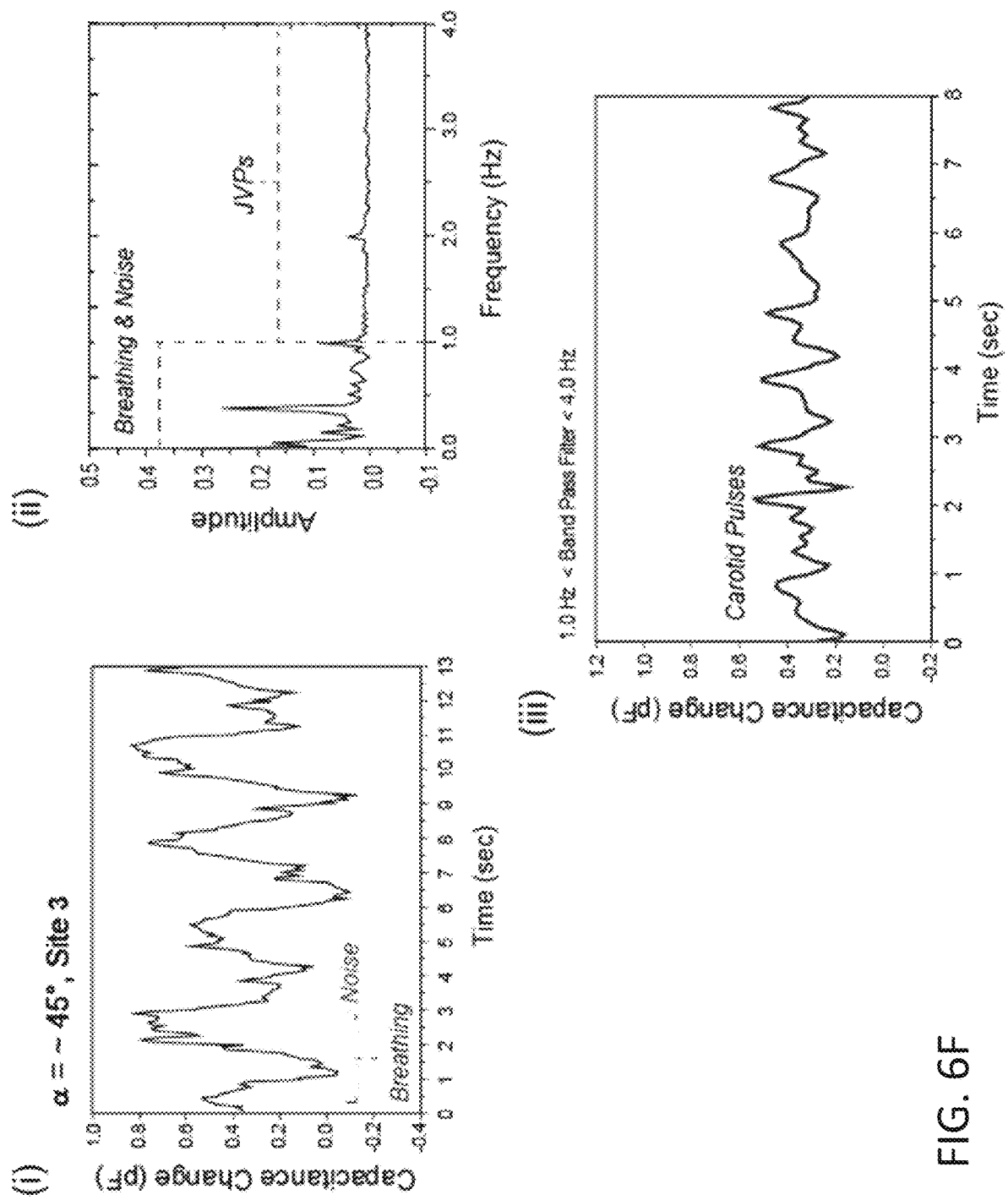
Figure 6G:
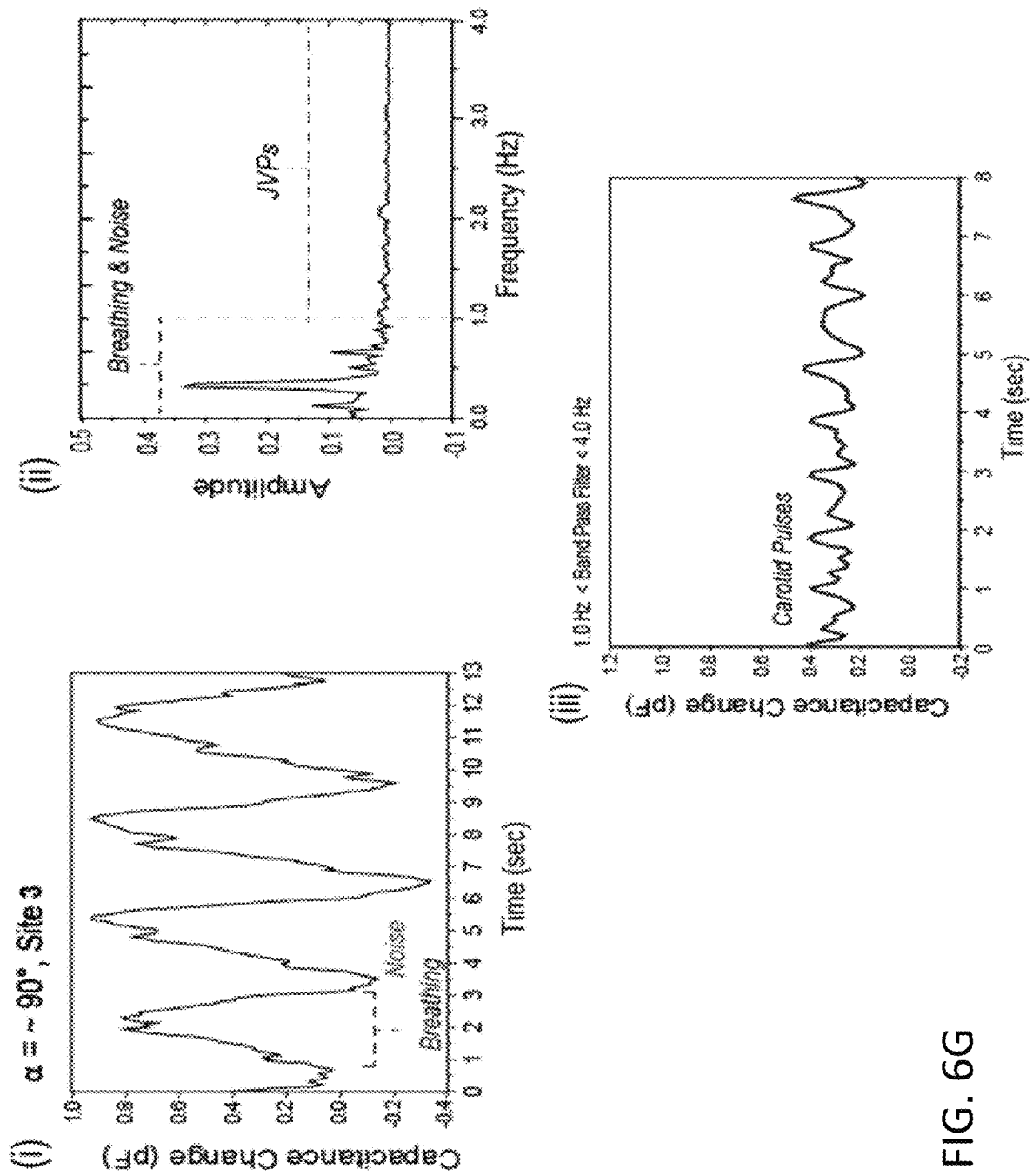

FIGS. 6A-6G show neck anatomy and measurements of pulses on identical contact sites of a neck of a subject with varying effective leaning angles. For example, to demonstrate the benefit of conformal contact for increased signal intensity, a sensor device as described herein can be used to measure pulses around a human neck. For instance, JVP signals can be observed in real-time and the measurements can be performed by placing the sensors on the subject's jugular veins, which are located approximately 3 centimeters vertical height above the sternal angle. The observation of JVP signals can be a non-invasive diagnostic method for exigent heart diseases as the JVP signals carry information about the internal jugular veins, such as cardiac filling pressure from right ventricular contraction, tricuspid valve, and right ventricular infarction. The JVP signals can be elevated with a raised venous pressure due to cardiac failure or hypervolaemia. However, the precise measurement of JVPs is difficult as the internal jugular veins are positioned rather deep inside of human necks and are easily affected by its surrounding external structures such as internal carotid artery, carotid sheath, and various nerves (FIG. 6B). In addition, even the subject's position during JVP measurement (e.g., lying down, sitting upright, or standing up) can influence the retrieved signals. Thus, conventional methods use sophisticated and expensive systems such as crystal microphones, cardiac MRI, or echocardiography. However, microhair sensor devices, in accordance with the present disclosure, can be a cheap, *facile* alternative.

FIG. 6A is a detailed illustration of monitoring pulse signals (carotid pulse or JVP) performed on three different contact sites on the neck (i.e., upper, middle, and lower region) with various effective leaning angles. A typical biphasic waveform of JVP consists of three upward and two downward deflections, which are correlated with the following cardiac mechanism: (1) the upward deflections are the "a" (atrial contraction), "c" (ventricular contraction and the resulting bulging of the tricuspid into the right atrium during isovolumetric systole), and "v" (atrial venous filling); (2) the downward deflections of the wave are the "x" (the atrium relaxes and the tricuspid valve moves downward) and the "y" descent (filling of the ventricle after tricuspid opening) (see FIG. 6A and Supplementary Information of Appendix B for detailed waveform and description of JVP biphasic waveforms). FIG. 6B illustrates example neck anatomy of the subject and an example biphasic waveform of jugular venous pulses.

FIGS. 6C-6G represent the capacitive responses of various physical forces including the waveforms, which can be measured from a healthy human subject (e.g., lacking any known cardiac diseases) and a cardiac-suffering patient, respectively. For the measurement performed on the healthy subject, the effective lying angle can be varied from approximately 5° to 90° to determine the optimal angle to provide the most accurate signal from three different regions on the subject's neck (sites 1, 2, and 3, FIG. 6A). The internal jugular vein of a patient can be extruded and can be visualized when the lying angle is approximately 45°. To remove the interference from breathing signal and precisely extract the carotid pulse signals and JVP waveforms from the retrieved data, the as-measured waveforms can be filtered by Fast Fourier Transform (FFT) with a band pass filter from 1.0 Hz to 4.0 Hz. This is also the unique frequency range of heart motion. In accordance with various embodiments, the microhair-structured pressure sensors can detect the difference in the pulsations of both the healthy and cardiac-suffering patients. Larger capacitance changes can be observed from the healthy subject's data than that of the cardiac-suffering subject, implying different physiologic conditions (e.g., respiration, carotid pulse, and JVPs).

Furthermore, the unique JVP-like waveforms can be obtained even when α is approximately 5° at site 3 for the healthy subject, whereas extruded JVPs may only be visually observed with a relatively higher lying angle of α~45° at sites 2 and 3 for the cardiac-suffering subject. The waveform of the healthy subject can be stable and uniform; whereas that obtained from the cardiac-suffering subject can be relatively unstable and with relatively low 'c' peaks and irregular 'v' peaks. Such characteristics can be associated with issues in the right tricuspid valve ('c' peak) and venous filling ('v' peak). As a reference, without the hairy structures on the flat sensor, JVP-shaped waveforms may not be detected.

FIG. 6A illustrates a detailed schematic of pulse monitoring using a micro-hairy pressure sensor on three different locations of the neck. FIG. 6B illustrates biphasic waveform of jugular venous pulses. FIGS. 6C-G, illustrate (each i) capacitive responses to various physical forces of a normal person, (each ii) Fourier Transformed data, and (each iii) the interpreted waveforms of carotid pulse and jugular venous pulses measured at (FIG. 6C) site 1 of α~5°, (FIG. 6D) site 2 of α~5°, (FIG. 6E) site 3 of α~5°, (FIG. 6F) site 3 of α~45°, and (FIG. 6G) site 3 of α~90°. Here, the interpreted waveforms of the carotid pulse and jugular venous pulse (each iii) can be filtered by Fast Fourier Transform (FFT) with band pass filter from 1.0 Hz to 4.0 Hz for unique relevant frequencies of carotid pulse and jugular venous pulse.

Thereby, embodiments in accordance with the present disclosure include flexible microhair structures to allow for conformal adhesion to skin. The high aspect ratio (AR 10) of the introduced microstructures can result in high sensitivity (approximately 0.58 $kPa^{-1}$) via effective contacts between the interface of the sensor device and the skin. In various embodiments, the sensor devices include wearable pressure sensors that allow for surprising detection of deep-lying pulse waveforms in addition to radial artery, respiration, and carotid pulses. By using a simple portable transmitter/receiver for wireless communication, the collected signals can be remotely monitored and distinguished for possible diagnostic purposes.

In accordance with a number of embodiments, the sensor devices can be formed of PEN/Cr/Au/PVA/PDMS/Au/Cr/PEN/PVA/microhair. For the bottom electrodes, a chromium layer (4 nm) followed by a gold (40 nm) layer can be thermally evaporated onto plasma-treated PEN substrates with a thickness of 12 µm. For the upper electrodes, pyramid-shaped microstructures (6 µm in width, 3 µm in height, and spacing of 3.8 µm) can be attached to the Au electrode using PVA (Sigma Aldrich, 40 mg of PVA/ml of DI water) as an adhesion layer between the Au layer and PDMS microstructures. For example, the pyramid microstructures can be fabricated by spin-coating 10-wt %-curing-agent-mixed PDMS onto a mold of pyramid microstructures at 5,000 rpm for 10 minutes. Then, the PDMS-coated mold can be laminated onto the PVA/Au/PEN substrate, which can be separately prepared by spin-coating PVA on the Au layer at 2,000 rpm for 1 minute, followed by heating the sample in an oven at 80° C. for at least 1 hour to evaporate the DI water in the PVA solution. After curing, the PDMS can be cured in the oven at 80° Celsius (C) for more than 30 minutes, the mold may be carefully delaminated by peeling back the PEN substrate, leaving behind a layer of PDMS with pyramid microstructures on the top electrode. For the bottom electrode, the microhair structures can be fabricated and attached to the PEN substrate, again using PVA as the adhesive layer. The method for attaching the PDMS microhair structures can be the same as above, except for using a different master mold. Before the assembly of the top and bottom electrodes (e.g., the upper portion and lower portion), each electrode can be connected with copper tape attached to 30 American Wire Gauge (AWG) wires. And, the two electrodes can be assembled together by pasting the PEN side of the top electrode to the center of a medical tape, and bringing the Au side of the bottom electrode to the exposed side (e.g., the side with PDMS pyramids) of the top electrode with alignment.

In a number of embodiments, the silicon master with nanoholes (e.g., 15 µm radius, AR=3, 6, and 10) can be prepared by photolithography and subsequent reactive ion etching. The master can be treated with a fluorinated-SAM solution ((tridecafluoro-1,1,2,2-tetrahydrooctyl)-trichlorosilane:FOTCS, Gelest Corp.) diluted to 0.03 molarity (M) in anhydrous heptane (Sigma Aldrich) in an Ar chamber. The surface-treated master can be annealed at 120° C. for 20 minutes.

To measure the change in capacitance and/or resistance as a function of the applied pressure, a wireless capacitance measurement system can be used. The system can include an AD7746 24 bit capacitance to digital converter (CDC) to interface with the sensor and collect the capacitance and/or resistance readings. A range extension circuit can be built for the CDC to allow for an input range of 0-116 picofarads (pF). An Arduino microcontroller (MCU) can be programmed to control the CDC and read sensor data at a rate of 90 Hz. By integrating an XBee Series 2 radio module to the MCU, sensor data can be wirelessly transmitted to a computer. The computer can perform software developed in the processing environment to receive, log, and output the sensor data to a visual display.

The capacitance and/or resistance measurements can be taken using an Agilent E4980A Precision LCR meter. Capacitances can be measured at the frequency of 1 kHz with a 1 V a.c. signal. A mechanized z-axis stage (Newmark Systems, 0.1 µm resolution) and a force gauge (Dillion GL model, 0.5 gram resolution) can be used to apply loads to the sensor pads on a probe station, all interfaced through a computer.

The sensor device can be attached to skin of a subject, such as on the wrist or on the neck. For JVP measurements, the effective lying angles can be varied using a chair or bed, and the sites of measurements were 3, 6, and 9 cm away from the subject's collarbone. The medical tape and the biocompatible polymer may be in contact with the subject's skin. Change in pressure can be measured by connecting the pressure sensor to a capacitance and/or resistance meter. The capacitance and/or resistance meter can record capacitive and/or resistance changes as a function of time for a period of time (e.g., no longer than 2 minutes). After measurements of the pulsation, the sensors can be disconnected from the meter and the medical tape can be carefully removed from the subject.

The "a" wave can corresponds to the contraction of the right atrial and it synchronously ends with the carotid artery pulse. The end of atrial systole is demarcated by the peak of the "a" wave. The "c" wave corresponds to the right ventricular contraction which causes the bulging of tricuspid valve towards the right atrium. The "x" descent following the "c" wave corresponds to the pulling of the tricuspid valve towards downward direction by the right ventricle, caused during the ventricular systole. It can be used to determine the degree of right ventricle contractility. The "v" wave corresponds to the filling of vein during the closure of the tricuspid valve and venous pressure increases from venous return, which occurs during and following the carotid pulse. Finally, the "y" descent corresponds to the opening of the tricuspid valve, thereby rapidly emptying the atrium into the ventricle.

The following references are hereby fully incorporated by reference for their teachings generally, and specifically for examples of further details regarding sensor devices and physiological parameters, and for reasons provided in this application and corresponding Appendices:

Kaltenbrunner, M. et al. An ultra-lightweight design for imperceptible plastic electronics. Nature 499, 458-463 (2013);

Kim, D. H. et al. Epidermal Electronics. Science 333, 838-843 (2011);

Webb, R. C. et al. Ultrathin conformal devices for precise and continuous thermal characterization of human skin. Nature Mater. 12, 938-944 (2013);

Salvatore, G. A. et al. Wafer-scale design of lightweight and transparent electronics that wraps around hairs. Nature Comm. 5, Article number: 2982 (2014);

Lee, S. et al. Ultrathin nanogenerators as self-powered/active skin sensors for tracking eye ball motion. Adv. Func. Mater. 24, 1163-1168 (2014);

Hammock, M. L., Chortos, A., Tee, B. C. K., Tok, J. B. H. & Bao, Z. A. 25th Anniversary Article: The evolution of electronic skin (E-Skin): a brief history, design considerations, and recent progress. Adv. Mater 25, 5997-6038 (2013);

Wang, C. et al. User-interactive electronic skin for instantaneous pressure visualization. Nature Mater. 12, 899-904 (2013);

Schwartz, G. et al. Flexible polymer transistors with high pressure sensitivity for application in electronic skin and health monitoring. Nature Comm. 4, Article number: 1859 (2013);

Kwak, M. K., Jeong, H. E. & Suh, K. Y. Rational design and enhanced biocompatibility of a dry adhesive medical skin patch. Adv. Mater 23, 3949-3953 (2011);

Yang, S. Y. et al. A bio-inspired swellable microneedle adhesive for mechanical interlocking with tissue. Nature Comm. 4, Article number: 1702 (2013);

Burrows, M. & Sutton, G. Interacting gears synchronize propulsive leg movements in a jumping insect. Science 341, 1254-1256 (2013);

Casas, J., Steinmann, T. & Krijnen, G. Why do insects have such a high density of flow-sensing hairs? Insights from the hydromechanics of biomimetic MEMS sensors. J. R. Soc. Interface. 7, 1487-1495 (2010);

Pang, C. et al. Bioinspired reversible interlocker using regularly arrayed high aspect-ratio polymer fibers. Adv. Mater 24, 475-479 (2012);

Lagarde, M. M. M., Drexl, M., Lukashkina, V. A., Lukashkin, A. N. & Russell, I. J. Outer hair cell somatic, not hair bundle, motility is the basis of the cochlear amplifier. Nature Neurosci. 11, 746-748 (2008);

Belanger, M. C. & Marois, Y. Hemocompatibility, biocompatibility, inflammatory and in vivo studies of primary reference materials low-density polyethylene and polydimethylsiloxane: A review. J Biomed Mater Res 58, 467-477 (2001);

Mittal, S. R., Garg, S. & Lalgarhia, M. Jugular venous pressure and pulse wave form in the diagnosis of right ventricular infarction. Int. J. Cardiol. 53, 253-256 (1996);

Haji, S. A. & Movahed, A. Right ventricular infarction—diagnosis and treatment. Clin. Cardiol. 23, 473-482 (2000);

Devine, P. J., Sullenberger, L. E., Bellin, D. A. & Atwood, J. E. Jugular venous pulse: window into the right heart. South. Med. J. 100, 1022-1027 (2007);

Pang, C. et al. A flexible and highly sensitive strain-gauge sensor using reversible interlocking of nanofibres. Nature Mater. 11, 795-801 (2012);

Pang, C., Kang, D., Kim, T. I. & Suh, K. Y. Analysis of preload-dependent reversible mechanical interlocking using beetle-inspired wing locking device. Langmuir 28, 2181-2186 (2012);

Waddell, T. K., Dart, A. M., Medley, T. L., Cameron, J. D. & Kingwell, B. A. Carotid pressure is a better predictor of coronary artery disease severity than brachial pressure. *Hypertension* 38, 927-931 (2001);

Pauca, A. L., Wallenhaupt, S. L., Kon, N. D. & Tucker, W. Y. Does radial artery pressure accurately reflect aortic pressure? *Chest* 102, 1193-1198 (1992);

Ewy, G. A. The abdominojugular test: technique and hemodynamic correlates. *Ann. Intern. Med.* 109, 456-460 (1988);

Eberlein-Konig, B. et al. Skin surface pH, stratum corneum hydration, trans-epidermal water loss and skin roughness related to atopic eczema and skin dryness in a population of primary school children. *Acta Derm.-Venereol.* 80, 188-191 (2000);

Lee, J. N., Jiang, X., Ryan, D. & Whitesides, G. M. Compatibility of mammalian cells on surfaces of poly(dimethylsiloxane). *Langmuir* 20, 11684-11691 (2004);

Craig, R. R. Mechanics of materials. (Wiley, 2011);

Kendall, K. Thin-film peeling—elastic term. *J. Phys. D. Appl. Phys.* 8, 1449-1452 (1975).

Conover, M. B. *Understanding electrocardiography.* (Mosby, 2002);

Tafur, E., Cohen, L. S. & Levine, H. D. The normal apex cardiogram: its temporal relationship to electrical, acoustic, and mechanical cardiac events. *Circulation* 30, 381-391 (1964);

Pittman, J. A. L., Ping, J. S. & Mark, J. B. Arterial and central venous pressure monitoring. *Int. Anesthesiol. Clin.* 42, 13-30 (2004);

Conover, M. B. *Understanding Electrocardiography.* (Mosby, 2002);

Devine, P. J., Sullenberger, L. E., Bellin, D. A. & Atwood, J. E. Jugular venous pulse: Window into the right heart. *South Med J* 100, 1022-1027 (2007); and Pauca, A. L., Wallenhaupt, S. L., Kon, N. D. & Tucker, W. Y. Does Radial Artery Pressure Accurately Reflect Aortic Pressure. *Chest* 102, 1193-1198, doi:DOI 10.1378/chest.102.4.1193 (1992);

Mannsfeld, S. C. B, Tee, B. C. K, Stoltenberg, R. M., Chenn, C. V. H. H, Barmann, S., Muir, B. V. O, Sokolov, A. N., Reese, C., Bao, Z. N., Highly Sensitive Flexible Pressure Sensors with Microstructured Rubber Dielectric layers, *Nature Materials* 9, 859-864 (2010);

Tee, B. C. K, Chortos, A., Dunn, R. R, Schwartz, G., Eason, E., Bao, Z., *Adv. Funct. Mater* 2014, 23, 5427;

Park, S., Kim, M, Vosgueritchian, M., Cheon, S., Kim, H, Koo, J. H., Kim, T. R., Lee, S, Schwartz, G., Chang, H., Bao, Z, *Adv. Mater,* 2014, DOI: 10.1002/adma.201402574;

Choong, C. L., Shim, M. B., Lee, B. S, Jeon, S., Ko, D. S., Kang, T. H., Bae, J., Lee, S. H., Byun, K. E., Im, J., Jeong, Y. J., Park, C. E., Park, J. J., Chung, U. I., *Adv. Mater.* 2014, 26, 3451; and Wang, X. W., Gu, Y., Xiong, Z. P., Cui, Z., Zhang, T., *Adv. Mater.* 2014, 26, 1336.

Further, the Appendices of the underlying provisional application are hereby fully incorporated by reference for their general and specific teachings: Appendix A entitled "Highly Skin-Conformal Microhairy Structures for Pulse Signal Amplification" and Appendix B entitled "Supplemental Information: Highly Skin-Conformal Microhairy Structures for Pulse Signal Amplification". Consistent with embodiments of the present disclosure, Appendix A describes and show examples of sensor devices and microstructures in accordance with the present disclosure. Appendix B describes and shows examples of experimental results of sensor devices and various microstructures, in accordance with the present disclosure.

As illustrated, various modules and/or other circuit-based building blocks (shown in the immediately preceding figure) may be implemented to carry out one or more of the operations and activities described herein or in the Appendices, and/or shown in the block-diagram-type figures. In such contexts, these modules and/or building blocks represent circuits that carry out one or more of these or related operations/activities. For example, in certain of the embodiments discussed above and in the Appendices, one or more modules and/or blocks are discrete logic circuits or programmable logic circuits configured and arranged for implementing these operations/activities, as in the circuit modules/blocks shown above and in the Appendices. In certain embodiments, the programmable circuit is one or more computer circuits programmed to execute a set (or sets) of instructions (and/or configuration data). Similarly, reference to the term "sensor" refers to a tangible and physical structure, that includes circuitry, and that responds to input from a physical environment (e.g., such as the skin to which the structure is secured) and then reacts to the input in a particular way as dictated by the circuitry. The instructions (and/or configuration data) can be in the form of firmware or software stored in and accessible from a memory (circuit). As an example, first and second modules/blocks include a combination of a CPU hardware-based circuit and a set of instructions in the form of firmware, where the first module/block includes a first CPU hardware circuit with one set of instructions and the second module/block includes a second CPU hardware circuit with another set of instructions.

Various embodiments described above, and discussed in the attached Appendices may be implemented together and/or in other manners. One or more of the items depicted in the present disclosure and in the Appendices can also be implemented separately or in a more integrated manner, or removed and/or rendered as inoperable in certain cases, as is useful in accordance with particular applications. In view of the description herein, those skilled in the art will recognize that many changes may be made thereto without departing from the spirit and scope of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

What is claimed is:

1. A sensor device, comprising:
    an upper portion including a plurality of layers, the plurality of layers including a layer with sensor circuitry and another layer having a plurality of upper-portion microstructures; and
    a lower portion including an electrically conductive layer configured and arranged to contact the plurality of upper-portion microstructures and including an array of lower-portion microstructures configured and arranged to interface with skin of a subject and to interlock or secure the skin with the sensor circuitry, the lower-portion microstructures characterized in that: each is flexible in response to engagement of the skin, and the array of lower-portion microstructures including microstructures characterized by geometrical and material properties and having an aspect ratio not greater than ten and not less than three, in terms of height and diameter, that manifests an ability of the lower portion microstructures to prevent buckling in response to an average radial artery force of 4 kPa being applied; wherein during operation of the sensor device the buckling is prevented in the presence of said average radial artery force corresponding to artery pulse waves of the subject, while the sensor circuitry senses the artery pulse waves.

2. The sensor device of claim 1, wherein the upper-portion microstructures and the sensor circuitry are further configured and arranged to measure data selected from: pulsations of venous pulses or arterial pulses of the subject, pulse waveforms of the subject, radial artery pulses of the subject, respiration of the subject, and carotid pulses of the subject, and a combination thereof.

3. The sensor device of claim 1, wherein: the plurality of upper-portion microstructures are further configured and arranged to enhance measurement of data selected from the group consisting of one of more of the following types of pressure: pressure pulses or waveforms that arise from venous pulses or arterial pulses of the subject, pulsations of venous pulses or arterial pulses of the subject, breathing, and a combination thereof, and wherein while the flexible lower-portion microstructures are in engagement with the skin, each of the lower-portion microstructures is asymmetrically shaped and configured to respond to said one of more of said types of pressure without buckling.

4. The sensor device of claim 1, further including circuitry configured and arranged to collect pressure data from the sensor circuitry, and a wireless transmitter configured and arranged to transmit the pressure data to a remote device, and the array of lower-portion microstructures include an adhesive portion to stick to the subject, wherein the lower-portion microstructures include microstructures having an aspect ratio of ten and a spacing ratio of three, thereby being configured and arranged to mitigate voids between the sensor device and the skin of the subject and to enhance a signal-to-noise ratio (SNR) via contact between the sensor device and the skin.

5. The sensor device of claim 1, wherein the plurality of upper-portion microstructures are pyramids in shape and have a height and a width of less than 100 μm and equal to or greater than three μm and are spaced apart by less than 100 μm, and the lower-portion microstructures have a height of 300 μm or less.

6. The sensor device of claim 1, wherein the lower-portion microstructures are microhair structures having a plurality of different heights and stiffness, wherein the microstructures of the lower portion are formed of polydimethysiloxane (PDMS).

7. The sensor device of claim 1, wherein the lower-portion microstructures are symmetric structures.

8. The sensor device of claim 1, wherein the microstructures of the upper portion and lower portion include conductive, insulative, or semiconductive materials.

9. The sensor device of claim 1, wherein the lower-portion microstructures are configured and arranged with spacings between adjacent ones of the lower-portion microstructures to enhance adhesion to the subject's skin, and the lower-portion microstructures include microstructures having an aspect ratio that is at least 6 and not greater than 10.

10. The sensor device of claim 1, wherein the lower-portion microstructures include microstructures having an aspect ratio that is 6 or 10.

11. The sensor device of claim 1, wherein the microstructures of the lower portion are uniformly distributed across the lower portion, and wherein the microstructures of the lower portion are of different heights.

12. The sensor device of claim 1, wherein the microstructures of the lower portion are non-uniformly distributed across the lower portion, and wherein the microstructures of the lower portion are of different heights.

13. The sensor device of claim 1, wherein each of the microstructures of the upper portion include a pyramid shape and have a height and width of less than 100 μm and equal to or greater than 3 μm and are spaced out by less than 100 μm and greater than or equal to 3.8 μm, and each of the microstructures of the lower portion include a tube shape and are between 300 μm and 90 μm in height, 30 μm in diameter and have a spacing ratio of 3.

14. The sensor device of claim 13, wherein the lower-portion microstructures include microstructures having an aspect ratio of 6 or 10 and a spacing ratio of 3, thereby being configured and arranged to mitigate voids between the sensor device and the skin of the subject and to enhance a signal-to-noise ratio (SNR) via contact between the sensor device and the skin.

15. The sensor device of claim 1, the array of lower-portion microstructures including microstructures being further characterized as the material properties including a certain weight percent of a curing agent material.

\* \* \* \* \*